US007920970B2

(12) United States Patent
Zuo et al.

(10) Patent No.: US 7,920,970 B2
(45) Date of Patent: Apr. 5, 2011

(54) METHODS AND APPARATUS FOR CHARACTERIZATION OF PETROLEUM FLUID AND APPLICATIONS THEREOF

(75) Inventors: Youxiang (Julian) Zuo, Edmonton (CA); Moin Muhammad, Katy, TX (US); Jiabao (Jack) Zhu, Edmonton (CA); Dingan (Dan) Zhang, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 3 days.

(21) Appl. No.: 12/209,050

(22) Filed: Sep. 11, 2008

(65) Prior Publication Data

US 2009/0192768 A1 Jul. 30, 2009

Related U.S. Application Data

(60) Provisional application No. 61/023,135, filed on Jan. 24, 2008.

(51) Int. Cl.
*G01V 1/40* (2006.01)
(52) U.S. Cl. ................................. 702/11; 702/6; 702/13
(58) Field of Classification Search ............... 73/152.24; 166/244.1, 336; 250/255, 269.1; 702/6–13; 703/10
See application file for complete search history.

(56) References Cited

U.S. PATENT DOCUMENTS

| 2,322,453 | A | * | 6/1943 | Kaveler ........................... 166/54 |
| 3,859,851 | A | | 1/1975 | Urbanosky |
| 4,994,671 | A | | 2/1991 | Safinya et al. |
| 5,167,149 | A | | 12/1992 | Mullins et al. |
| 5,201,220 | A | | 4/1993 | Mullins et al. |
| 5,266,800 | A | | 11/1993 | Mullins |
| 5,331,156 | A | | 7/1994 | Hines et al. |
| 6,101,447 | A | * | 8/2000 | Poe, Jr. ........................... 702/13 |
| 6,108,608 | A | | 8/2000 | Watts, III |
| 7,081,615 | B2 | | 7/2006 | Betancourt et al. |
| 7,249,009 | B2 | | 7/2007 | Ferworn et al. |
| 7,289,943 | B2 | | 10/2007 | Barroux |
| 2002/0016703 | A1 | | 2/2002 | Barroux |
| 2004/0104341 | A1 | | 6/2004 | Betancourt et al. |
| 2007/0119244 | A1 | | 5/2007 | Goodwin et al. |
| 2007/0143023 | A1 | | 6/2007 | Betancourt et al. |

FOREIGN PATENT DOCUMENTS

| WO | WO99/42937 A1 | 8/1999 |
| WO | WO2006/020952 A2 | 2/2006 |

OTHER PUBLICATIONS

Thiery et al., 'Individual Characterization of Petroleum Fluid Inclusions (compositions and P-T Traping conditions) by microthermometery and confocal laser scanning microscopy inferences from applied thermodynamics of oils', Sep. 30, 2002, Marine and Petroleum Geology, pp. 847-859.*

(Continued)

*Primary Examiner* — Michael P Nghiem
*Assistant Examiner* — Elias Desta
(74) *Attorney, Agent, or Firm* — Jay P. Sbrollini; Wayne I. Kanak

(57) ABSTRACT

An improved method and system for characterizing the compositional components of a hydrocarbon reservoir of interest and analyzing fluid properties of the reservoir of interest based upon its compositional components.

27 Claims, 10 Drawing Sheets

OTHER PUBLICATIONS

Aasberg-Petersen, Kim et al: "Prediction of Viscosities of Hydrocarbon Mixtures", Fluid Phase Equilibria, 1991, vol. 70, pp. 293-308.
Alboudwarej, H. et al: "Effective Tuning of Wax Precipitation Models", 7th International Conference on Petroleum Phase Behavior and Fouling, Asheville, North Carolina, Jun. 25-29, 2006.
Almehaideb, Reyadh A. et al: "EOS tuning to model full field crude oil properties using multiple well fluid PVT analysis", Journal of Petroleum Science and Engineering, 2000, vol. 26, pp. 291-300.
Behrens, R.A. et al: "The Use of Semicontinuous Description to Model the C7+ Fraction in Equation of State Calculations", SPE Reservoir Engineering, Aug. 1988, pp. 1041-1047.
Betancourt, S.S. et al: "Exploration Applications of Downhole Measurement of Crude Oil Composition and Fluorescence", Asia Pacific Technical Conference 2003, SPE 87011.
Chorn, Larry G. et al: "C7 Fraction Characterization", Advances in Thermodynamics, vol. 1, 1989 Taylor & Francis New York Inc., pp. 35-56.
Christensen, P.L.: "Regression to Experimental PVT Data", Journal of Canadian Petroleum Technology, Special Edition 1999, vol. 38, No. 13, Paper: 96-10-15, pp. 1-9.
Coats, K.H. et al: "Application of a Regression-Based EOS PVT Program to Laboratory Data", SPE Reservoir Engineering, May 1986, pp. 277-299.
Cotterman, Ronald L. et al: "Flash Calculations for Continuous or Semicontinuous Mixtures Using an Equation of State", Ind. Eng. Chem. Process Des. Dev., 1985, vol. 24, pp. 434-443.
Cotterman, Ronald L. et al: "Phase Equilibria for Mixtures Containing Very Many Components. Development and Application of Continuous Thermodynamics for Chemical Process Design", Ind. Eng. Chem. Process Des. Dev., 1985, vol. 24, pp. 194-203.
Du, James L. et al: "A Thermodynamic Model for the Prediction of Asphaltene Precipitation", Petroleum Science and Technology, 2004, vol. 22, Nos. 7 & 8, pp. 1023-1033.
Dubost, F. et al: "Integration of In-Situ Fluid Measurements for Pressure Gradients Calculations", Society of Petroleum Engineers, 2007, SPE 108494.
Firoozabadi, A.: "Thermodynamics of Hydrocarbon Reservoirs", McGraw Hill, 1999.
Fujisawa, G. et al: "Large Hydrocarbon Compositional Gradient Revealed by In-Situ Optical Spectroscopy", Society of Petroleum Engineers ATCE Houston, Sep. 2004, SPE 89704.
Ghorayeb, Kassem et al: "Interpretation of the Unusual Fluid Distribution in the Yufutsu Gas-Condensate Field", SPE Journal, Jun. 2003, pp. 114-123.
Ghorayeb, K. et al: "Modeling Multicomponent Diffusion and Convection in Porous Media", SPE Journal, 2000, 5(2), pp. 158-171.
Ghorayeb, Kassem et al: "Molecular, Pressure, and Thermal Diffusion in Nonideal Multicomponent Mixtures", AIChE Journal, May 2000, vol. 46, No. 5, pp. 883-891.
Ghorayeb, K. et al: "Numerical Study of Natural Convection and Diffusion in Fractured Porous Media", SPE Journal, 2000, 5(1), pp. 12-20.
Gonzalez, D.L. et al: "Prediction of Asphaltene Instability under Gas Injection with the PC-SAFT Equation of State", Energy * Fuels, 2005, vol. 19, pp. 1230-1234.
Guo, X.-Q. et al: "Viscosity model based on equations of state for hydrocarbon liquids and gases", Fluid Phase Equilibria 139, 1997, pp. 405-421.
Hirschberg, Avraham: "Role of Asphaltenes in Compositional Grading of a Reservoir's Fluid Column", Journal of Petroleum Technology, Jan. 1988, pp. 89-94.
Hoffmann, A.E. et al: "Equilibrium Constants for a Gas-Condensate System", Society of Petroleum Engineers, 1953, vol. 198, SPE 219-G, pp. 1-10.
Hoier, Lars et al: "Compositional Grading—Theory and Practice", Society of Petroleum Engineers, Oct. 2000, pp. 1-16, SPE 63085.
Jhaveri, Bharat S. et al: "Three-Parameter Modification of the Peng-Robinson Equation of State to Improve Volumetric Predictions", Society of Petroleum Engineers, August 1988, SPE 13118, pp. 1033-1040.
Kabir, C.S. et al: "How Reliable is Fluid Gradient in Gas/Condensate Reservoirs", Society of Petroleum Engineers, 2006, SPE 99386.
Katz, D.L. et al: "Predicting Phase Behavior of Condensate/Crude-Oil Systems Using Methane Interaction Coefficients", Society of Petroleum Engineers, Nov. 1978, SPE 6721, pp. 1649-1655.
Kesler, Michael G. et al: "Improve prediction of enthalpy of fractions", Hydrocarbon Processing, Mar. 1976, pp. 153-158.
Lohrenz, John et al: "Calculating Viscosities of Reservoir Fluids From Their Compositions", Society of Petroleum Engineers, Oct. 1964, SPE 915, pp. 1171-1176.
Manafi, Hussain et al: "Phase behavior prediction of petroleum fluids with minimum characterization data", Journal of Petroleum Science & Engineering, 1999, vol. 22, pp. 67-93.
Montel, Francois et al : "Initial state of petroleum reservoirs: a comprehensive approach", Journal of Petroleum Science & Engineering, Mar. 12, 2006, pp. 391-402.
Montel, Francois et al: "Modeling the Effect of External Gas Flux on Reservoir Fluid Distribution", Society of Petroleum Engineers, Sep.-Oct. 2002, pp. 1-6, SPE 77383.
Montel, Francois et al: "Prediction of Compositional Grading in a Reservoir Fluid Column", Society of Petroleum Engineers, Sep. 1985, pp. 1-12, SPE 14410.
Montel, Francois et al: "Pressure and Compositional Gradients in Reservoirs", Society of Petroleum Engineers, Aug. 2003, pp. 1-8, SPE 85668.
Mullins, O. et al: "Asphaltene Gravitational Gradient in a Deepwater Reservoir as Determined by Downhole Fluid Analysis", Society of Petroleum Engineers, Houston 2007, SPE 106375.
Nasrabadi, H. et al: "Reservoir Initialization in Two-Phase Hydrocarbon Reservoirs from Well PVT Data", Society of Petroleum Engineers, 2005, SPE 95804.
Pedersen, K.S. et al: "Characterization of Gas Condensate Mixtures", C7 Fraction Characterization, Advances in Thermodynamics, vol. 1, 1989 Taylor & Francis New York Inc. pp. 137-151.
Pedersen, K.S. et al: "Modeling of Large Hydrocarbon Compositional Gradient", Society of Petroleum Engineers, Nov. 2006, pp. 1-7, SPE 101275.
Pedersen, K.S. et al: "Simulations of Compositional Gradients in Hydrocarbon Reservoirs Under the Influence of a Temperature Gradient", Society of Petroleum Engineers, Oct. 2003, pp. 1-10, SPE 84364.
Peneloux et al: "A Consistent Correction for Redlich-Kwong-Soave Volumes", Fluid Phase Equilibria, 1982, vol. 8, pp. 7-23.
Peng, D.-Y et al: "A New Two-Constant Equation of State", Ind. End. Chem. Fundam., 1976, vol. 15, pp. 59-64.
Ratulowski, J. et al: "Theoretical and Experimental Investigation of Isothermal Compositional Grading", SPE Reservoir Evaluation & Engineering, Jun. 2003, pp. 168-175.
Riazi, Mohammad R. et al: "Prediction of the Composition of Petroleum Fractions", Ind. Eng. Chem. Process Des. Dev. 1980, vol. 19, pp. 289-294.
Schulte, A.M.: "Compositional Variations Within a Hydrocarbon col. due to Gravity", Society of Petroleum Engineers of AIME, Sep. 1980, pp. 1-10, 9235.
Shorter Communications: "An improved corresponding states model for the prediction of oil and gas viscosities and thermal conductivities", Chemical Engineering Science, 1987, vol. 42, No. 1, pp. 182-186.
Soave, G.: "Equilibrium Constants from a Modified Redlich-Kwong Equation of State", Chemical Engineering Science, 1972, vol. 27, pp. 1197-1203.
Twu, Chorng H.: "An Internally Consistent Correlation for Predicting the Critical Properties and Molecular Weights of Petroleum and Coal-Tar Liquids", Fluid Phase Equilibria, 1984, vol. 16, pp. 137-150.
Whitson, Curtis H. et al: "Application of the Gamma Distribution Model to Molecular Weight and Boiling Point Data for Petroleum Fractions", Chem. Eng. Comm. 1990, vol. 96, pp. 259-278.
Whitson, Curtis H.: "Characterizing Hydrocarbon Plus Fractions", Society of Petroleum Engineers, Aug. 1983 SPE 12233, pp. 683-694.
Whitson, Curtis H.: "Effect of C7 Properties on Equation-of-State Predictions", Society of Petroleum Engineers Journal, Dec. 1984, pp. 685-696.

Zuo, Julian Youxiang et al: "An improved thermodynamic model for wax precipitation from petroleum fluids", Chemical Engineering Science 56 (2001) pp. 6941-6947.

Almehaideb, Reyadh A. et al: "EOS tuning to model full field crude oil properties using multiple well fluid PVT analysis", Journal of Petroleum Science and Engineering, 2000, vol. 26, pp. 291-300.

Malik, Mayank et al: "Field Examples of History Matching of Formation-Tester Measurements Acquired in the Presence of Oil-Based Mud-Filtrate Invasion", SPWLA 48th Annual Logging Symposium, Jun. 3-6, 2007, pp. 1-16.

Ng, Heng-Joo et al: "Hydrate Formation in Systems Containing Methane, Ethane, Propane, Carbon Dioxide or Hydrogen Sulfide in the Presence of Methanol", Fluid Phase Equilibria, 1985, vol. 21, pp. 145-155.

Ng, Heng-Joo et al: "New Developments in the Measurements and Prediction of Hydrate Formation for Processing Needs", International Conference on Natural Gas Hydrates, 1994, vol. 715, pp. 450-462.

Ng, Heng-Joo et al: "The Measurement and Prediction of Hydrate Formation in Liquid Hydrocarbon-Water Systems", Ind. Eng. Chem., Fundam., 1976, vol. 15, No. 4, pp. 293-298.

Nichita, Dan Vladimir et al: "Pseudocomponent Delumping for Multiphase Systems with Waxy Solid Phase Precipitation", Energy & Fuels, 2008, vol. 22, pp. 775-783.

Pederson, K.S. et al: "Properties of Oils and Natural Gases", Contributions in Petroleum Geology & Engineering, vol. 5, 1989, Gulf Publishing Company.

Technische Universitat Hamburg-Harburg: "Appendix A2: Mixing Rules for Simple EOS", Thermische Verfahrenstechnik, http://www.tu-harburg.de/vt2/pe2000 Dokumentation/PE2000_Kap8A2.htm.

Zuo, Julian Youxiang et al: "A Thermodynamic Model for Gas Hydrates in the Presence of Sales and Methanol", Chem. Eng. Comm., 2001, vol. 184, pp. 175-192.

Zuo, Julian Youxiang et al: "Hydrate Phase Equilibrium Calculations for Crude Oils", 5th International Conference on Gas Hydrates Jun. 13-16, 2005, Trondheim, Norway 7.

Zuo, Julian Youxiang et al: "Plus Fraction Characterization and PVT Data Regression for Reservoir Fluids near Critical Conditions", Society of Petroleum Engineers Asia Pacific Oil and Gas Conference and Exhibition, Brisbane, Australia, Oct. 16-18, 2000, SPE 64520.

Zuo, Julian Youxiang et al: "Prediction of Gas Hydrate Formation Conditions in Aqueous Solutions of Single and Mixed Electrolytes", SPE Journal, Dec. 1997, vol. 2, SPE 31048, pp. 406-416.

Zuo, Julian Youxiang et al: "Representation of Hydrate Phase Equilibria in Aqueous Solutions of Methanol and Electrolytes Using an Equation of State", Energy & Fuels, 2000, vol. 14(1), pp. 1-12.

Zuo, Julian Youxiang et al: "Wax Formation from Synthetic Oil Systems and Reservoir Fluids", Energy & Fuels 2008, vol. 22, pp. 2390-2395.

* cited by examiner

METHODS AND APPARATUS FOR CHARACTERIZATION OF PETROLEUM FLUID AND APPLICATIONS THEREOF

CROSS-REFERENCE TO RELATED APPLICATION

This application claims priority from U.S. Provisional Application 61/023,135, filed Jan. 24, 2008, which is incorporated herein by reference.

BACKGROUND OF THE INVENTION

1. Field of the Invention

The present invention relates to methods and apparatus for characterizing petroleum fluid extracted from a hydrocarbon bearing geological formation. The invention has application to reservoir simulation applications, although it is not limited thereto.

2. Description of Related Art

Petroleum consists of a complex mixture of hydrocarbons of various molecular weights, plus other organic compounds. The exact molecular composition of petroleum varies widely from formation to formation. The proportion of hydrocarbons in the mixture is highly variable and ranges from as much as 97% by weight in the lighter oils to as little as 50% in the heavier oils and bitumens. The hydrocarbons in petroleum are mostly alkanes (linear or branched), cycloalkanes, aromatic hydrocarbons, or more complicated chemicals like asphaltenes. The other organic compounds in petroleum typically contain carbon dioxide ($CO_2$), nitrogen, oxygen, and sulfur, and trace amounts of metals such as iron, nickel, copper, and vanadium.

The alkanes, also known as paraffins, are saturated hydrocarbons with straight or branched chains which contain only carbon and hydrogen and have the general formula $C_nH_{2n+2}$. They generally have from 5 to 40 carbon atoms per molecule, although trace amounts of shorter or longer molecules may be present in the mixture. The alkanes include methane ($CH_4$), ethane ($C_2H_6$), propane ($C_3H_8$), i-butane ($iC_4H_{10}$), n-butane ($nC_4H_{10}$), i-pentane ($iC_5H_{12}$), n-pentane ($nC_5H_{12}$), hexane ($C_6H_{14}$), heptane ($C_7H_{16}$), octane ($C_8H_{18}$), nonane ($C_9H_{20}$), decane ($C_{10}H_{22}$), hendecane ($C_{11}H_{24}$)— also referred to as endecane or undecane, dodecane ($C_{12}H_{26}$), tridecane ($C_{13}H_{28}$), tetradecane ($C_{14}H_{30}$), pentadecane ($C_{15}H_{32}$), and hexadecane ($C_{16}H_{34}$).

The cycloalkanes, also known as napthenes, are saturated hydrocarbons which have one or more carbon rings to which hydrogen atoms are attached according to the formula $C_nH_2n$. Cycloalkanes have similar properties to alkanes but have higher boiling points. The cycloalkanes include cyclopropane ($C_3H_6$), cyclobutane ($C_4H_8$), cyclopentane ($C_5H_{10}$), cyclohexane ($C_6H_{12}$), cycloheptane ($C_7H_{14}$), etc.

The aromatic hydrocarbons are unsaturated hydrocarbons which have one or more planar six-carbon rings called benzene rings, to which hydrogen atoms are attached with the formula $C_nH_n$. They tend to burn with a sooty flame, and many have a sweet aroma. Some are carcinogenic. The aromatic hydrocarbons include benzene ($C_6H_6$) and derivatives of benzene, as well as polyaromatic hydrocarbons.

Computer-based modeling and simulation techniques have been developed for estimating the properties and/or phase behavior of petroleum fluid in a reservoir of interest. Typically, such techniques employ an equation of state (EOS) model that represent the phase behavior of the petroleum fluid in the reservoir. Once the EOS model is defined, it can be used to compute a wide array of properties of the petroleum fluid of the reservoir, such as gas-oil ratio (GOR) or condensate-gas ratio (CGR), density of each phase, volumetric factors and compressibility, and heat capacity and saturation pressure (bubble or dew point). Thus, the EOS model can be solved to obtain saturation pressure at a given temperature. Moreover, GOR, CGR, phase densities, and volumetric factors are byproducts of the EOS model. Other properties, such as heat capacity or viscosity, can also be derived in conjunction with the information regarding fluid composition. Furthermore, the EOS model can be extended with other reservoir evaluation techniques for compositional simulation of flow and production behavior of the petroleum fluid of the reservoir, as is well known in the art. For example, compositional simulations can be helpful in studying (1) depletion of a volatile oil or gas condensate reservoir where phase compositions and properties vary significantly with pressure below bubble or dew point pressures, (2) injection of non-equilibrium gas (dry or enriched) into a black oil reservoir to mobilize oil by vaporization, and (3) injection of $CO_2$ into an oil reservoir to mobilize oil by miscible displacement and by oil viscosity reduction and oil swelling.

The data that describes the heavier hydrocarbon components (i.e., alkanes such as propane, butane, pentane, hexane, heptane and heavier) of the petroleum fluid is important to the accuracy of the EOS model and the results that are derived therefrom. Typically, characterization of the heavier hydrocarbon components includes a delumping process carried out on compositional data measured from fluid samples captured by a well logging tool. The compositional data describes the concentrations (and possibly other properties) of the low order hydrocarbon components (typically methane and ethane) of the petroleum fluid as well as the concentration (and possibly other properties) of component groups of the petroleum fluid. For example, such component groups can include the C3-C5 alkane group (propane, butane, and pentane) and groups of heavier alkane components (C6+). The delumping process operates on the compositional data measured from fluid samples captured by a well logging tool to estimate molar distribution of the components of the component groups. For example, Whitson in "Characterizing Hydrocarbon Plus Fractions," *Society of Petroleum Engineers Journal*, 1983, pp. 683-694, employs a probabilistic distribution model to derive mole fractions for alkane components of the C7+ group. Weight fractions for such components are then derived from molecular weights and the derived mole fractions. However, the Whitson approach cannot handle the delumping of the C3-C5 alkane group and cannot convert weight fractions of the reservoir fluids to the mole fractions which are required in the EOS modeling because of the unknown molecular weight of the C6+ fraction. In another example, Pedersen et al. in "Characterization of Gas Condensate Mixtures," American Institute of Chemical Engineers Spring National Meeting, March 1988, Technical Paper 36C, New Orleans, La., USA, American Institute of Chemical Engineers, 1988, pp. 137-151, employs an empirical formula to derive mole fractions for single carbon number alkane components of the C7+ group. The empirical formula includes constants that are specific to the actual mixture under evaluation. However, like the Whitson approach, the Pedersen approach cannot handle the delumping of the C3-C5 alkane group and cannot convert weight fractions of the reservoir fluids to mole fractions. Pedersen et al. assume that the mole fractions heavier than C7 follow an exponential distribution versus carbon number, which is sometimes inaccurate for a well logging tool. Therefore, the present invention assumes that the weight fractions instead of the mole fractions heavier than C7 follow an exponential distribution versus carbon number, and better results have been obtained.

An example of a well logging tool suitable for capturing fluid samples for compositional data analysis is the Modular Dynamic Formation Tester (MDT) tool, available from Schlumberger Technology Corporation of Sugar Land, Tex., USA. The MDT tool provides a controlled channel of hydraulic communication between the reservoir fluid and the wellbore and allows withdrawal of small amounts of formation fluid through a probe that contacts the reservoir rock (formation). Such downhole fluid sampling is advantageous because the sampling is more accurate downhole. More specifically, in the event that the sampling pressure is above the saturation pressure, the fluid will be in a single phase ensuring that the original composition is being analyzed. For pressures below the saturation pressure, a measurement of the properties of the liquid phase in the oil zone and the associated gas above it will yield a more accurate sampling than a sample recombined at the surface. Indeed, it may be difficult to retain the sample in the state in which it existed downhole when it is retrieved to surface. Historically, fluid samples collected by well logging tools were brought to the surface for analysis in the laboratory. However, recent developments in the MDT tool have made possible the direct measurement of fluid properties downhole during the pump-out or sampling sequence, which is referred to herein as "downhole fluid analysis (DFA)." Details of the MDT tool and its capabilities for downhole fluid analysis may be obtained with reference to U.S. Pat. Nos. 3,859,851; 4,994,671; 5,167,149; 5,201,220; 5,266,800; and 5,331,156, all of which are incorporated herein by reference.

The variation of hydrocarbon components amongst petroleum samples dictates the characteristics of the particular sample. Typically, petroleum samples are classified into fluid types that include black oils, volatile oils, retrograde condensates, wet gases, and dry gases. These fluid types require different considerations for their exploitation, and different properties are used for their description. For example, it is generally agreed that black oils and dry gases can be described satisfactorily using averaged properties of the oil and gas phases, such as the volumetric factors and gas solubility ratios. Volatile oils, retrograde condensates, and wet gases require a more detailed knowledge of the fluid composition since the ultimate recovery will be dictated by the control of the production conditions (mostly pressure).

Downhole fluid analysis is advantageous because information is provided in real time, in contrast to a laboratory analysis that may require several days, or surface wellsite analysis that may result in undesirable phase transitions as well as the loss of key constituents. A detailed description of the fluid properties is desirable for an accurate modeling of the fluids in the reservoir. Indeed, decisions such as the type of well completion, production procedures, and the design of the surface handling and processing facilities are affected by the characteristics of the produced fluids.

BRIEF SUMMARY OF THE INVENTION

Therefore, the invention provides methods and apparatus for characterizing reservoir fluid in a manner that accurately reflects the heavier hydrocarbon components of the reservoir fluid.

The invention further provides methods and apparatus for characterizing reservoir fluids in a manner that accounts for thermodynamic behavior of the reservoir fluids.

The invention also provides methods and apparatus for compositional analysis of reservoir fluids in conjunction with thermodynamic behavior of the reservoir fluids.

Accordingly, a method and apparatus for characterizing one or more properties of a multi-component petroleum fluid stores data representing at least one property for a group of components of the multi-component petroleum fluid. At least one property for the respective components of the group is derived from the stored data and an empirical relation derived from analysis of a pressure-volume-temperature (PVT) database. The property(ies) of the respective components of the group is (are) used to estimate or predict one or more properties of the fluid. In the illustrative embodiment, the property (ies) for the group of components includes weight percentage of a group of alkane components, and the property(ies) for the respective components of the group include weight percentages for respective alkane components of the group. The empirical relation preferably follows a linear function of carbon number for the respective alkane components of the group as described herein.

In the illustrative embodiment, the PVT database stores weight percentage, molecular weight, molar percentage, specific gravity of single carbon number alkane components ($CO_2$, C1, C2 . . . C30+), as well as PVT properties (for example GOR, API gravities, formation volume factor (FVF), densities, and viscosities) for a large number of samples (e.g., on the order of 100 samples) from different petroleum reservoirs throughout the world.

In the preferred embodiment, at least one property (e.g., weight percentage) for at least one particular component of the multi-component petroleum fluid can be derived from the property (e.g., weight percentage) for a respective component of the group and an empirical relation derived from analysis of the PVT database.

In another example, molecular weight for at least one particular component of the multi-component petroleum fluid is derived by an empirical relation based on GOR data. Specific gravity for the particular component is derived from the molecular weight.

The property(ies) for the particular components of the fluid can be used to generate an equation of state model for predicting one or more properties of said multi-component fluid such as i) PVT properties (such as phase envelope, pressure-temperature (PT) flash, constant composition expansion (CCE), differential liberation (DL), constant volume depletion (CVD), separation, viscosity, oil and gas formation volume factors (FVF) and compressibility factor); ii) compositional and property gradients; iii) gas hydrate formation; iv) wax precipitation; v) asphaltene precipitation; and v) scaling.

In the preferred embodiment, the method and apparatus employ a downhole sampling tool. Downhole data acquired with the downhole sampling tool is used to derive initial data for the compositional analysis of the reservoir fluid as described herein.

Additional objects and advantages of the invention will become apparent to those skilled in the art upon reference to the detailed description taken in conjunction with the provided figures.

DETAILED DESCRIPTION OF THE INVENTION

Figure 1:
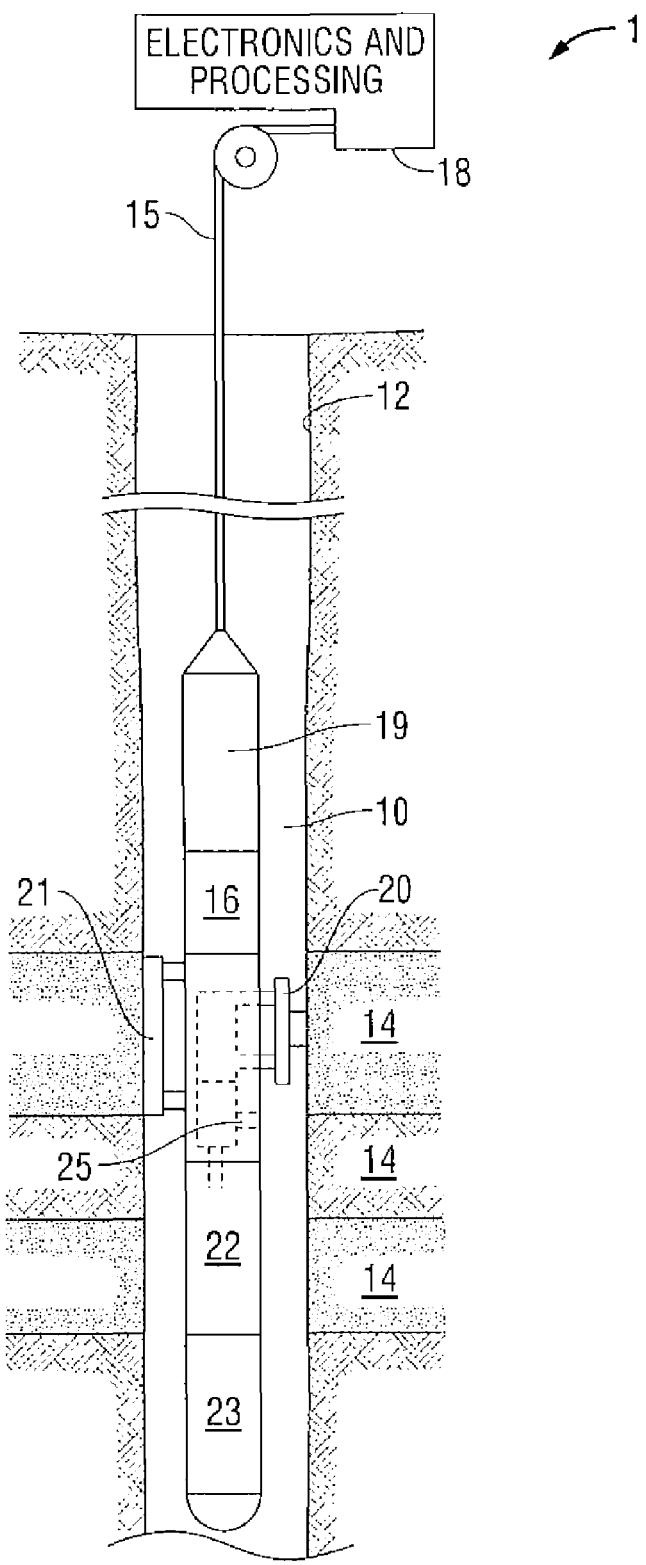
FIG. 1 is a schematic diagram of an exemplary petroleum reservoir analysis system in which the present invention is embodied.

FIG. 1 illustrates an exemplary petroleum reservoir analysis system 1 in which the present invention is embodied. The system 1 includes a borehole tool 10 suspended in the borehole 12 from the lower end of a typical multiconductor cable 15 that is spooled in a usual fashion on a suitable winch (not shown) on the formation surface. The cable 15 is electrically coupled to an electrical control system 18 on the formation surface. The tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the tool body. The fluid admitting assembly 20 is equipped for selectively sealing off or isolating selected portions of the wall of the borehole 12 such that pressure or fluid communication with the adjacent earth formation 14 is established. Also included with tool 10 are means for determining the downhole pressure and temperature (not shown) and a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly 20, the fluid analysis module 25, and the flow path to the collecting chambers is maintained by the control systems 16 and 18. As will be appreciated by those skilled in the art, the surface-located electrical control system 18 includes data processing functionality (e.g., one or more microprocessors, associated memory, and other hardware and/or software) to implement the invention as described herein. The electrical control system 18 can also be realized by a distributed data processing system wherein data measured by the tool 10 is communicated (preferably in real time) over a communication link (typically a satellite link) to a remote location for data analysis as described herein. The data analysis can be carried out on a workstation or other suitable data processing system (such as a computer cluster or computing grid).

Figure 2A:
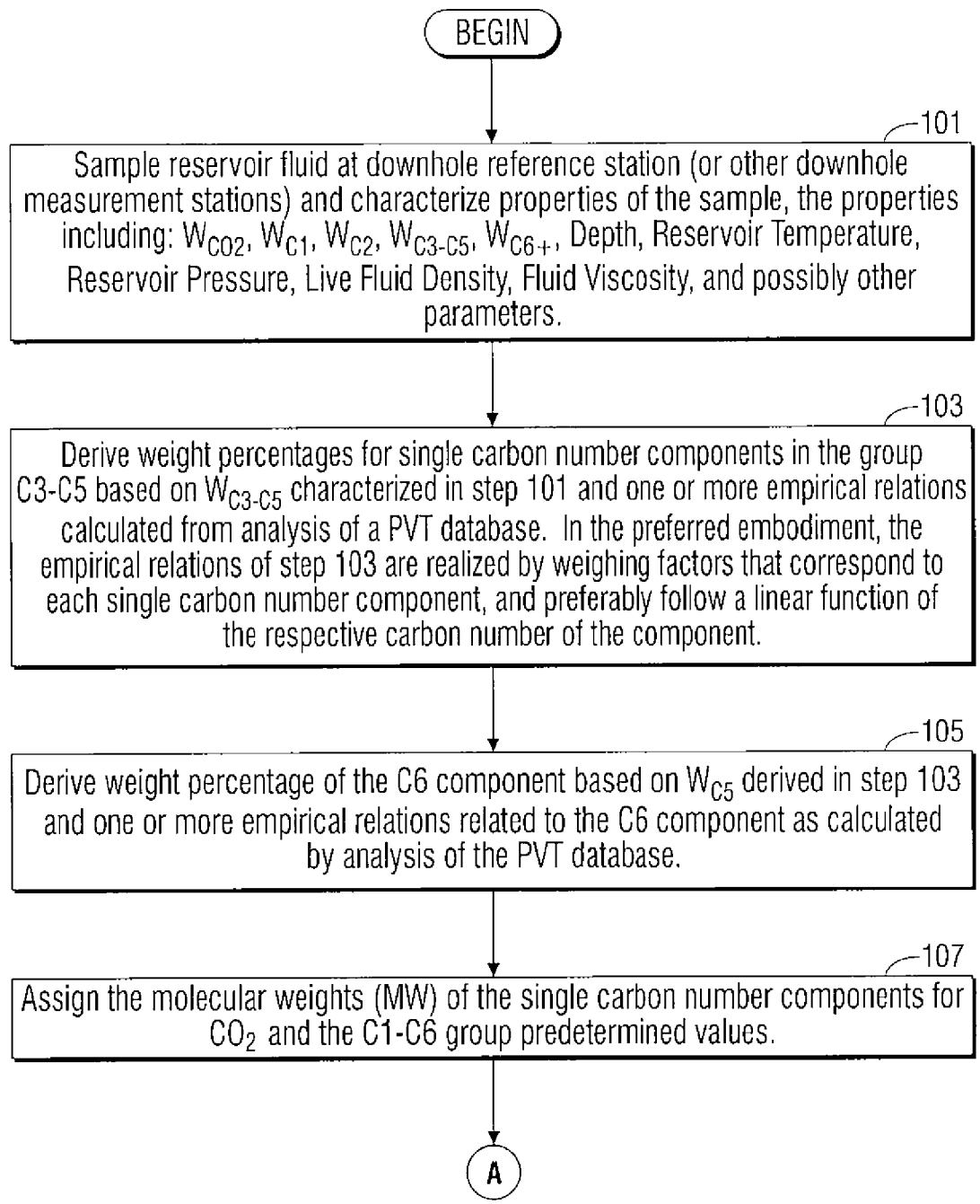
FIGS. 2A-2C, collectively, are a flow chart of data analysis operations for characterizing the compositional components of a reservoir of interest and analyzing fluid properties of the reservoir of interest based upon its compositional components.
Figure 2B:
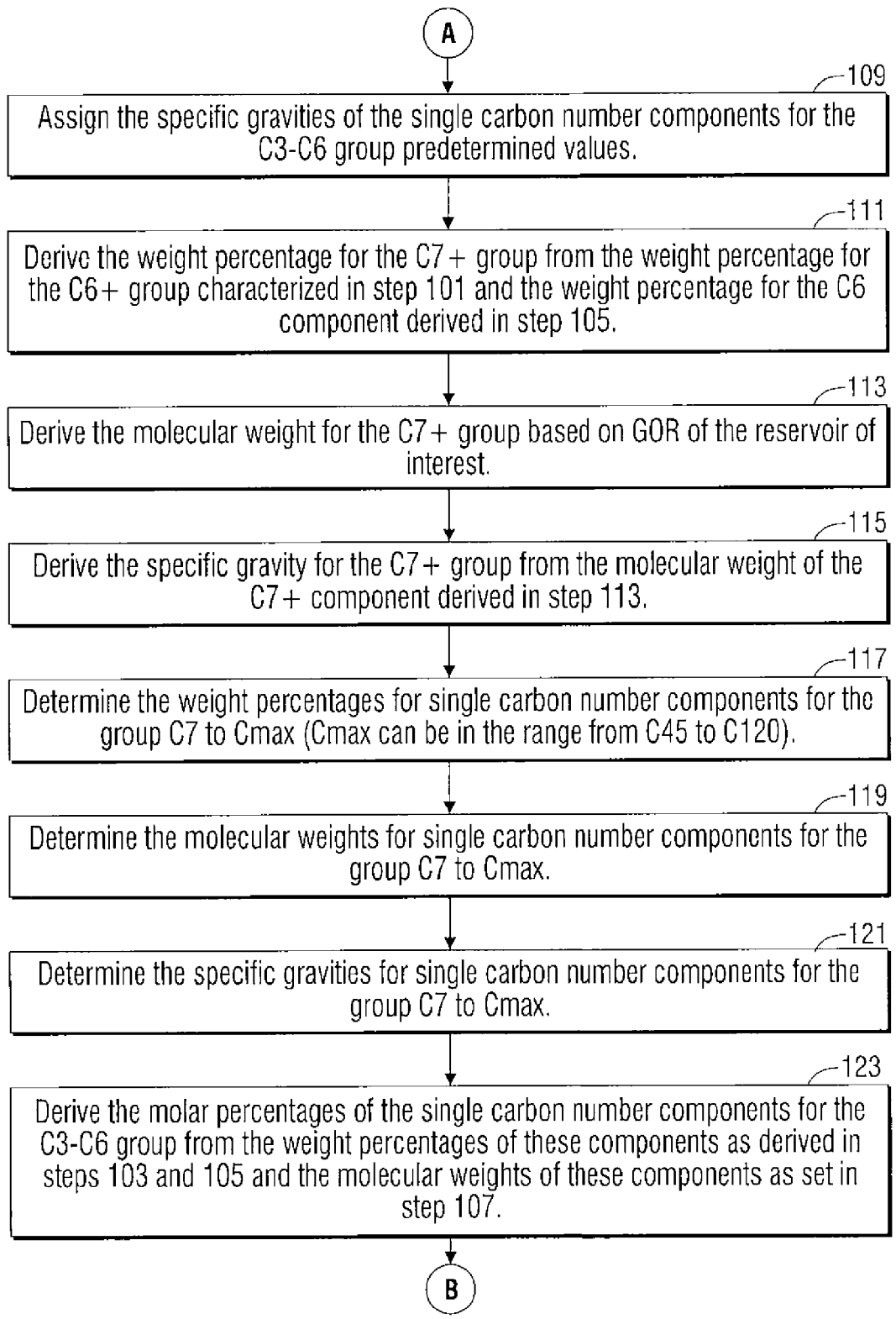
Figure 2C:
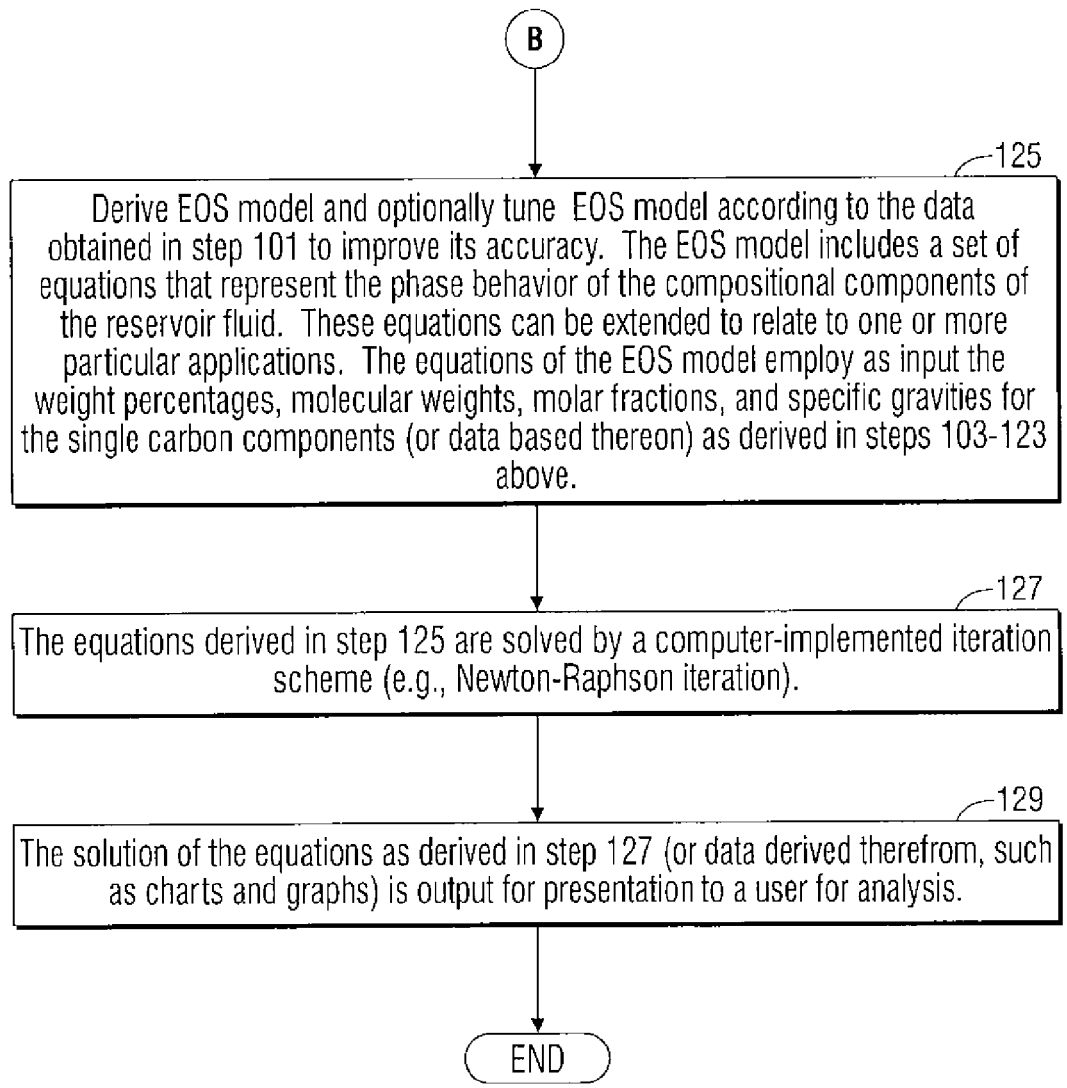
Figure 3:
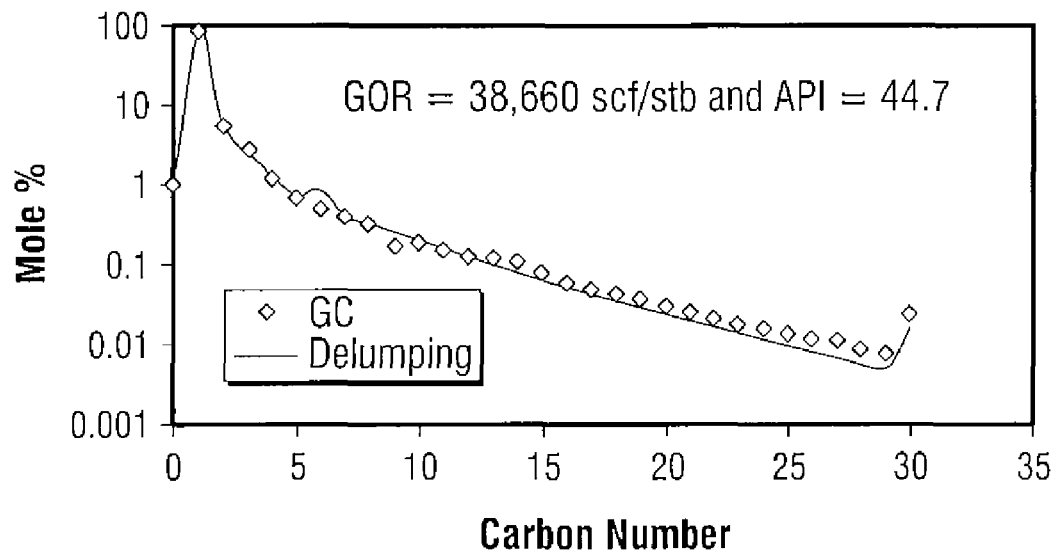
FIGS. 3-7 are graphs that illustrate results of the reservoir fluid compositional analysis methodology described herein as compared to lab-measured gas chromatography (GC) data for different fluid types.
Figure 4:
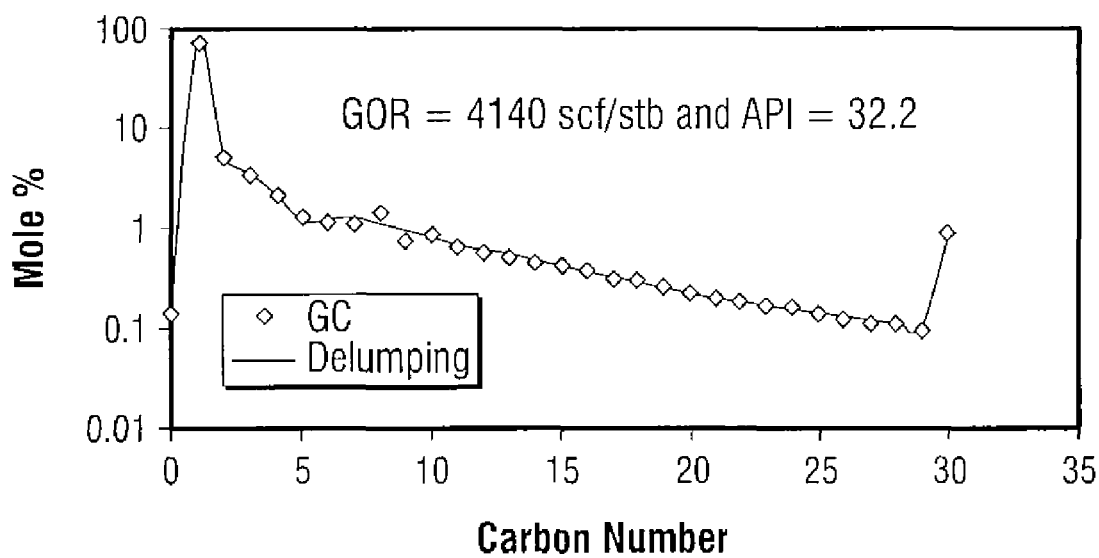
Figure 5:
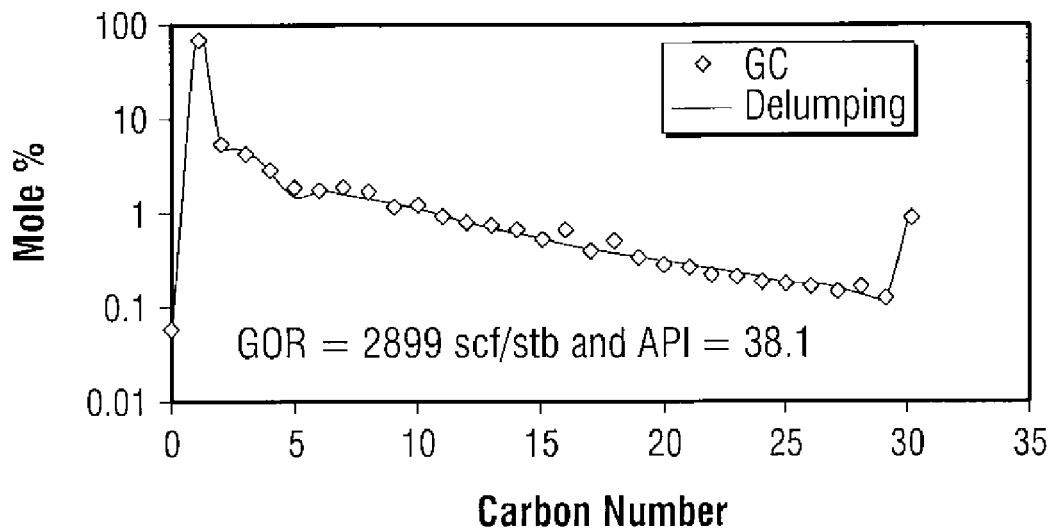
Figure 6:
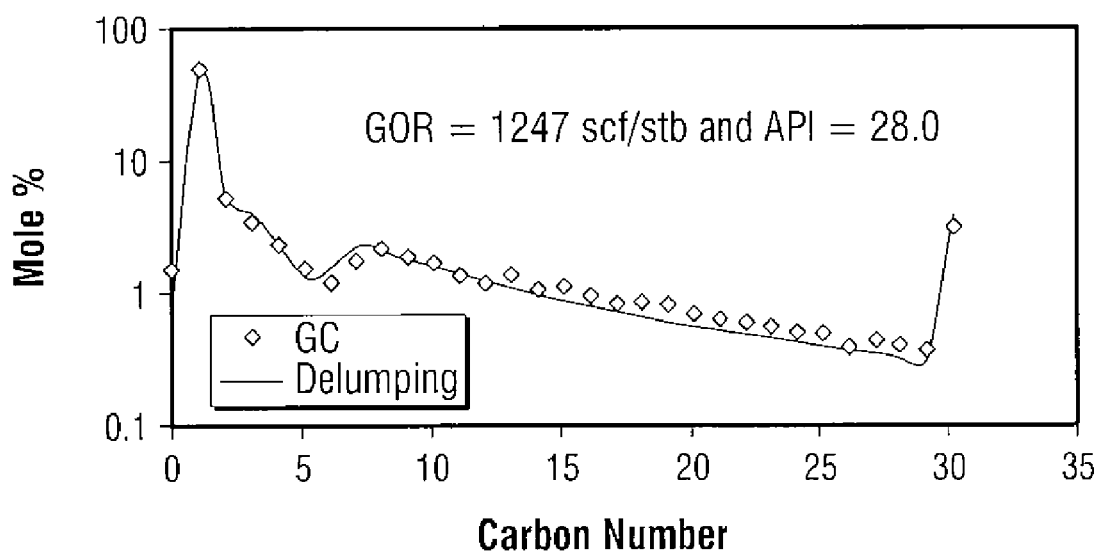
Figure 7:
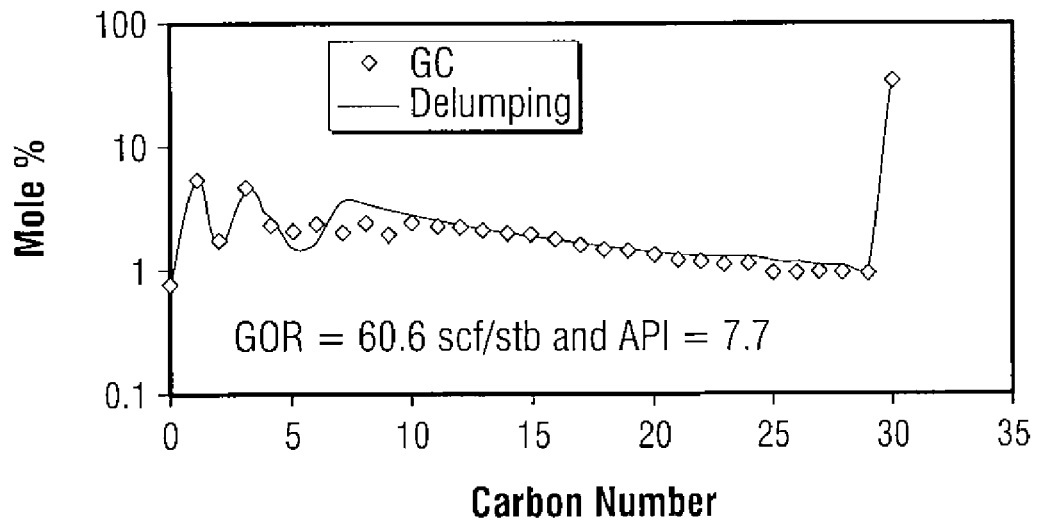

In accordance with the present invention, the apparatus of FIG. 1 is employed with the methodology of FIGS. 2A-2C to characterize the compositional components of a reservoir of interest and analyze fluid properties of the reservoir of interest based upon its compositional components. In step 101, a sample of reservoir fluid is obtained at one or more reference stations within the borehole 12 at the reservoir pressure and temperature. The sample is processed by the fluid analysis module 25. In the preferred embodiment, the fluid analysis module 25 measures absorption spectra and translates such measurements into concentrations of several alkane components and groups in the fluids of interest. In an illustrative embodiment, the fluid analysis module 25 provides measurements of the concentrations (e.g., weight percentages) of carbon dioxide ($CO_2$), methane ($CH_4$), ethane ($C_2H_6$), the C3-C5 alkane group including propane, butane, and pentane, and the lump of hexane and heavier alkane components (C6+). The weight percentage of $CO_2$ is labeled $W_{CO2}$. The weight percentage of methane ($CH_4$) is labeled $W_{C1}$. The weight percentage of ethane ($C_2H_6$) is labeled $W_{C2}$. The weight percentage for the group of alkanes with 3 to 5 carbon atoms (referred to as C3-C5) is labeled $W_{C3-C5}$. The C3-C5 alkane group includes propane, butane, and pentane. The weight percentage for the group of alkanes with 6 or more carbon atoms (referred to as C6+) is labeled $W_{C6+}$. The C6+ alkane group includes hexane ($C_6H_{14}$), heptane ($C_7H_{16}$), octane ($C_8H_{18}$), nonane ($C_9H_{20}$), decane ($C_{10}H_{22}$), hendecane ($C_{11}H_{24}$)— also referred to as endecane or undecane, dodecane ($C_{12}H_{26}$), tridecane ($C_{13}H_{28}$), tetradecane ($C_{14}H_{30}$), pentadecane ($C_{15}H_{32}$), hexadecane ($C_{16}H_{34}$), etc. The tool 10 also provides a means to measure temperature of the fluid sample (and thus reservoir temperature at the reference station), pressure of the fluid sample (and thus reservoir pressure at the reference station), live fluid density of the fluid sample, fluid viscosity, gas-oil ratio (GOR) of the fluid sample, API gravity of the fluid sample, and formation volume factor (FVF) of the fluid sample.

In step 103, weight percentages for the single carbon number alkane components (propane, butane, and pentane) within the C3-C5 group are derived from the weight percentage for the C3-C5 alkane group ($W_{C3-C5}$) characterized in step 101 and one or more empirical relations related to such components as calculated by analysis of a database of fluid properties for samples from a number of reservoirs (referred to herein as "PVT database").

In the illustrative embodiment, the PVT database stores weight percentage, molecular weight, molar percentage, specific gravity of single carbon number alkane components ($CO_2$, C1, C2 . . . C30+), as well as pressure-volume-temperature (PVT) properties (for example GOR, API gravities, FVF, densities, viscosities) for a large number of samples (e.g., on the order of 100 samples) from different petroleum reservoirs throughout the world.

In the preferred embodiment, the empirical relations related to the alkane components of the C3-C5 group follow a linear distribution function as follows:

$$\psi_i = A*CN_i + B \quad (1)$$

where i varies from 3 to 5, $\psi_i$ is the weighing factor for the $i^{th}$ single carbon alkane component in the group C3-C5, and $CN_i$ is the carbon number for the $i^{th}$ single carbon number alkane component in the group C3-C5.

Regression analysis can be carried out over the weight percentages for the C3 to C5 alkane components stored in the PVT database to fit such weight percentages to Equation (1). The parameters A and B are given by the results of such regression analysis. In an illustrative embodiment, parameter A falls within the range from −0.2 to 0.2 and parameter B falls within the range of 0.1 to 1.5. Having derived A and B, the weighing factors for the single carbon number alkane components of the group C3-C5 are determined by Equation (1). The weighing factors $\psi_i$ are then normalized by the following equation:

$$\psi'_i = \psi_i \bigg/ \sum_{i=3}^{5} \psi_i \qquad (2)$$

where $\psi'_i$ are the normalized weighing factors for the single carbon alkane components of the group C3-C5.

The weight percentages for the single carbon number alkane components of the group C3-C5 are determined by the equation:

$$W_{Ci} = \psi'_i W_{C3-C5} \qquad (3)$$

The calculation of the normalized weighing factors $\psi'_i$ for the single carbon number alkane components of the group C3-C5 is preferably performed prior to the sampling of step 101 (possibly on another computer processing system) and saved for subsequent access during step 103 as described herein. In this scenario, the regression analysis that is carried out on the PVT database is performed prior to the sampling of step 101 (possibly on another computer processing system) and the resultant data (the normalized weighing factors $\psi'_i$) is saved for subsequent access during step 103 as described herein. In the same way, C2-C5 can be delumped into C2, C3, C4, and C5 if a well logging tool provides the weight percentage of the C2-C5 alkane group.

In step 105, weight percentage for the C6 alkane component (hexane) is derived from the weight percentage for the C5 alkane component ($W_{C5}$) as determined in step 103 and one or more empirical relations related to the C6 alkane component as calculated by analysis of the PVT database.

In the preferred embodiment, the empirical relation related to the C6 alkane component is represented by the following equation:

$$W_{C6} = C^* W_{C5} \qquad (4)$$

Regression analysis can be carried out over the weight percentages for the C5 and C6 alkane components stored in the PVT database to fit such weight percentages to Equation (4). The parameter C is given by the results of such regression analysis. In an illustrative embodiment, the parameter C falls within the range from 0.1 to 3. Having derived C, the weight percentage for the C6 alkane component (hexane) is derived from Equation (4). The calculation of the parameter C is preferably performed prior to the sampling of step 101 (possibly on another computer processing system) and saved for subsequent access during step 105 as described herein. In this scenario, the regression analysis that is carried out on the PVT database is performed prior to the sampling of step 101 (possibly on another computer processing system) and the resultant data (the parameter C) is saved for subsequent access during step 105 as described herein.

In step 107, the molecular weights (MW) of $CO_2$ and the single carbon number alkane components for the C1-C6 group are assigned predetermined values. In the preferred embodiment, such assignment is as follows:
  $MW_{CO2}$=44.01 g/mol;
  $MW_{C1}$=16.04 g/mol;
  $MW_{C2}$=30.07 g/mol;
  $MW_{C3}$=44.10 g/mol;
  $MW_{C4}$=58.12 g/mol;
  $MW_{C5}$=72.15 g/mol; and
  $MW_{C6}$=84.00 g/mol.

These molecular weights can be found in the *Handbook of Physical Chemistry*, 88th Edition, 2007-2008, CRC Press.

In step 109, the specific gravities (SG) of the single carbon number alkane components for the $C_3$-$C_6$ group are assigned predetermined values. In the preferred embodiment, such assignments are as follows:
  $SG_{C3}$=0.5825 g/mol;
  $SG_{C4}$=0.6141 g/mol;
  $SG_{C5}$=0.6215 g/mol; and
  $SG_{C6}$=0.7096 g/mol.

These specific gravities can be found in the *Handbook of Physical Chemistry*, 88th Edition, 2007-2008, CRC Press.

In step 111, the weight percentage for the C7+ alkane group is derived from the weight percentage for the C6+ alkane group ($W_{C6+}$) measured in step 101 and the weight percentage for the C6 alkane component ($W_{C6}$) derived in step 105 as follows:

$$W_{C7+} = W_{C6+} - W_{C6} \qquad (5)$$

In step 113, the molecular weight (MW) for the C7+ alkane group is derived based on the GOR of the reservoir of interest.

In the preferred embodiment, the GOR of the reservoir of interest is obtained in step 101. When the GOR obtained in step 101 is in the range between 10 scf/stb and 10,000 scf/stb, GOR is related to the molecular weight for the C7+ alkane group ($MW_{C7+}$) by the following equation:

$$MW_{C7+} = \alpha_1 * GOR^{\alpha_2} \qquad (6)$$

The parameters $\alpha_1$ and $\alpha_2$ are preferably derived by regression analysis carried out over the PVT database. In an illustrative embodiment, the parameter $\alpha_1$ is in the range between 500 and 1000 and the parameter $\alpha_2$ is in the range between −0.2 to 0.2. Having derived parameters $\alpha_1$ and $\alpha_2$, the molecular weight for the C7+ alkane group can be derived from Equation (6). The calculations of the parameters $\alpha_1$ and $\alpha_2$ are preferably performed prior to the sampling of step 101 (possibly on another computer processing system) and saved for subsequent access during step 115 as described herein. In this scenario, the regression analysis that is carried out on the PVT database is performed prior to the sampling of step 101 (possibly on another computer processing system) and the resultant data (the parameters $\alpha_1$ and $\alpha_2$) is saved for subsequent access during step 113 as described herein.

When the GOR obtained in step 101 is less than 10 scf/stb, GOR is related to the molecular weight for the C7+ alkane group ($MW_{C7+}$) by the following equation:

$$MW_{C7+} = \beta_1 * GOR + \beta_2 \qquad (7)$$

The parameters $\beta_1$ and $\beta_2$ are preferably derived by regression analysis carried out over the PVT database. In an illustrative embodiment, parameter $\beta_1$ is in the range between −10 to 10 and parameter $\beta_2$ is in the range between 0 and 1000. Having derived parameters $\beta_1$ and $\beta_2$, the molecular weight for the C7+ alkane group can be derived from Equation (7). The calculations of the parameters $\beta_1$ and $\beta_2$ are preferably performed prior to the sampling of step 101 (possibly on another computer processing system) and saved for subsequent access during step 113 as described herein. In this scenario, the regression analysis that is carried out on the PVT database is performed prior to the sampling of step 101 (possibly on another computer processing system) and the resultant data (the parameters $\beta_1$ and $\beta_2$) is saved for subsequent access during step 113 as described herein.

Alternatively (for example, for cases where the GOR for the reservoir of interest is not obtained in step 101), the GOR for the reservoir of interest can be estimated by empirical relation derived from correlation over the PVT database.

In one example, GOR is related to the weight percentages of the C1 alkane component and C6+ alkane group as follows:

$$GOR = \gamma_1 \frac{W_{C1}}{W_{C6+} - \beta_3 W_{C1}} \quad (8)$$

In this example, the parameters $\gamma_1$ and $\beta_3$ are derived by correlating the GOR data to the $W_{C1}$ and $W_{C6+}$ values in the PVT database. In an illustrative embodiment, parameters $\gamma_1$ and $\beta_3$ are in the range between 5000 and 10000 and 0.1 and 0.4, respectively. Having derived parameters $\gamma_1$ and $\beta_3$, an estimate for the GOR of the reservoir of interest can be derived from Equation (8). This GOR estimate can then be used to derive the $MW_{C7+}$ according to Equations (6) or (7). The calculations of the parameters $\gamma_1$ and $\beta_3$ are preferably performed prior to the sampling of step 101 (possibly on another computer processing system) and saved for subsequent access during step 113 as described herein. In this scenario, the regression analysis that is carried out on the PVT database is performed prior to the sampling of step 101 (possibly on another computer processing system) and the resultant data (the parameters $\gamma_1$ and $\beta_3$) is saved for subsequent access during step 113 as described herein.

In another example, GOR can be related to the weight percentages of the C1 alkane component, C2-C5 alkane group, $CO_2$ component, and C6+ alkane group as follows:

$$GOR = \gamma_2 \frac{\gamma_3 W_{C1} + \gamma_4 W_{C2-5} + \gamma_5 W_{CO2}}{W_{C6+}} \quad (9)$$

In this example, the parameters $\gamma_2$, $\gamma_3$, $\gamma_4$, $\gamma_5$ are derived by correlating the GOR data to the $W_{CO2}$, $W_{C1}$, $W_{C2-5}$, and $W_{C6+}$ values in the PVT database. In an illustrative embodiment, the parameters $\gamma_2$, $\gamma_3$, $\gamma_4$, $\gamma_5$ are in the range between 5000 and 12,000, 0.5 and 1.0, 0.1 and 0.4, and 0.1 and 0.4, respectively. Having derived parameters $\gamma_2$, $\gamma_3$, $\gamma_4$, $\gamma_5$, an estimate for the GOR of the reservoir of interest can be derived from Equation (9). This GOR estimate can then be used to derive the $MW_{C7+}$ according to Equations (6) or (7). The calculations of the parameters $\gamma_2$, $\gamma_3$, $\gamma_4$, $\gamma_5$ are preferably performed prior to the sampling of step 101 (possibly on another computer processing system) and saved for subsequent access during step 113 as described herein. In this scenario, the regression analysis that is carried out on the PVT database is performed prior to the sampling of step 101 (possibly on another computer processing system) and the resultant data (the parameters $\gamma_2$, $\gamma_3$, $\gamma_4$, $\gamma_5$) is saved for subsequent access during step 113 as described herein.

In step 115, the specific gravity (SG) of the C7+ alkane group is derived from the molecular weight of the C7+ alkane group derived in step 113. In the preferred embodiment, $SG_{C7+}$ is related to the $MW_{C7+}$ by the following equation:

$$SG_{C7+} = \eta_1 \ln(MW_{C7+}) + \eta_2 \quad (10)$$

In this example, the parameters $\eta_1$, $\eta_2$ can be derived by regression analysis carried out over the PVT database. In an illustrative embodiment, $\eta_1, \eta_2$ are each in the range between 0 and 0.3. The calculations of the parameters $\eta_1, \eta_2$ are preferably performed prior to the sampling of step 101 (possibly on another computer processing system) and saved for subsequent access during step 115 as described herein. In this scenario, the regression analysis that is carried out on the PVT database is performed prior to the sampling of step 101 (possibly on another computer processing system) and the resultant data (the parameters $\eta_1, \eta_2$) is saved for subsequent access during step 115 as described herein.

In step 117, weight percentages for single carbon number alkane components C7 to Cmax are determined. In the preferred embodiment, Cmax is in the range between C45 and C120. Such weight percentages can be related to carbon number Ci according to the following equations:

$$\ln W_{Ci} = D + E * CNi \quad (11)$$

$$\sum_{i=C7}^{Cmax} W_{Ci} = \sum_{i=C7}^{Cmax} D + E * CNi = W_{C7+} \quad (12)$$

$$\sum_{i=C7}^{Cmax} \frac{W_{Ci}}{MW_{Ci}} = \sum_{i=C7}^{Cmax} \frac{D + E * CNi}{MW_{Cj}} = \frac{W_{C7+}}{MW_{C7+}} \quad (13)$$

The parameters D and E can be derived by solving Equations (12) and (13). Having derived parameters D and E, the weight percentages for single carbon number alkane components C7 to Cmax can be derived from Equation (11).

In step 119, molecular weight (MW) for single carbon number alkane components C7 to Cmax are determined. The molecular weight (MW) for the single carbon number alkane components C7 to C45 can be set from the values in the third column of Table 1 below. The molecular weight (MW) for the single carbon number alkane components beyond C45 is given by the following equation:

$$MW_{Ci} = 14 CN_i - 4 \quad (14)$$

In step 121, the specific gravities for single carbon number alkane components C7 to Cmax are determined. The SG's for the single carbon number alkane components C7 to C45 are listed in column 2 of Table 1 below.

TABLE 1

| Hydrocarbon Group | Specific Gravity | Molecular Weight (g/mol) |
| --- | --- | --- |
| C7  | 0.722 | 96  |
| C8  | 0.745 | 107 |
| C9  | 0.764 | 121 |
| C10 | 0.778 | 134 |
| C11 | 0.789 | 147 |
| C12 | 0.800 | 161 |
| C13 | 0.811 | 175 |
| C14 | 0.822 | 190 |
| C15 | 0.832 | 206 |
| C16 | 0.839 | 222 |
| C17 | 0.847 | 237 |
| C18 | 0.852 | 251 |
| C19 | 0.857 | 263 |
| C20 | 0.862 | 275 |
| C21 | 0.867 | 291 |
| C22 | 0.872 | 305 |
| C23 | 0.877 | 318 |
| C24 | 0.881 | 331 |
| C25 | 0.885 | 345 |
| C26 | 0.889 | 359 |
| C27 | 0.893 | 374 |
| C28 | 0.896 | 388 |
| C29 | 0.899 | 402 |

TABLE 1-continued

| Hydrocarbon Group | Specific Gravity | Molecular Weight (g/mol) |
|---|---|---|
| C30 | 0.902 | 416 |
| C31 | 0.906 | 430 |
| C32 | 0.909 | 444 |
| C33 | 0.912 | 458 |
| C34 | 0.914 | 472 |
| C35 | 0.917 | 486 |
| C36 | 0.919 | 500 |
| C37 | 0.922 | 514 |
| C38 | 0.924 | 528 |
| C39 | 0.926 | 542 |
| C40 | 0.928 | 556 |
| C41 | 0.930 | 570 |
| C42 | 0.931 | 584 |
| C43 | 0.933 | 598 |
| C44 | 0.935 | 612 |
| C45 | 0.937 | 626 |

The specific gravity (SG) for the single carbon number alkane components beyond C45 is given by the following equation:

$$SG_{Ci} = D_1 \ln(MW_{Ci}) + D_2 \quad (15)$$

$$\sum_{i=C7}^{Cmax} \frac{W_{Ci}}{\sum_{j=C7}^{Cmax} \frac{W_{Cj}}{SG_{Ci}}} = \sum_{i=C7}^{Cmax} \frac{D + E * CNi}{\sum_{j=C7}^{Cmax} \frac{D + E * CNj}{D_1 \ln(MW_{Cj}) + D_2}} = SG_{C7+} \quad (16)$$

The known specific gravity and molecular weight for a single carbon number alkane component (such as the C6 alkane component) can be used in Equation (15) along with Equation (16) to solve for $D_1$ and $D_2$. After solving for $D_1$ and $D_2$, the specific gravity (SG) for the single carbon number alkane components beyond C45 is given by Equation (15).

In step 123, the molar percentages (MP) of all components are derived from the weight percentages of these components as derived in steps 103 and 105 and the molecular weights (MW) of these components as set in step 107.

In the preferred embodiment, the molar percentages (MP) of all components are derived as follows:

$$MP_{Ci} = \frac{\frac{W_{Ci}}{MW_{Ci}}}{\sum_{i=1}^{Max} \left(\frac{W_{Ci}}{MW_{Ci}}\right)} \quad (17)$$

In step 125, an EOS model is derived and, optionally, tuned according to the data obtained in step 101 to improve its accuracy. The EOS model includes a set of equations that represent the phase behavior of the compositional components of the reservoir fluid. The equations can be extended to relate to one or more particular applications as described below in more detail. The equations derived in step 125 employ as input the weight percentages, molecular weights (MWs), and specific gravities (SGs) for the single carbon number alkane components (or data based thereon) as derived in steps 103-123 above.

The equations of the EOS model of step 125 can take many forms. For example, they can be any one of many cubic EOS, as is well known. Such cubic EOS include van der Waals EOS (1873), Redlich-Kwong EOS (1949), Soave-Redlich Kwong EOS (1972), Peng-Robinson EOS (1976), Stryjek-Vera-Peng-Robinson EOS (1986), and Patel-Teja EOS (1982). Volume shift parameters can be employed as part of the cubic EOS in order to improve liquid density predictions, as is well known. Mixing rules (such as van der Waals mixing rule) can also be employed as part of the cubic EOS. A statistical associating fluid theory, SAFT-type, EOS can also be used, as is well known in the art. Tuning of the EOS model typically involves tuning volume translation parameters, binary interaction parameters, and/or critical properties of the components of the EOS model. An example of EOS tuning is described in Reyadh A. Almehaideb et al., "EOS tuning to model full field crude oil properties using multiple well fluid PVT analysis," *Journal of Petroleum Science and Engineering*, Volume 26, Issues 1-4, pp. 291-300, 2000, incorporated herein by reference in its entirety.

In step 125, the equations of the EOS model can be extended for particular application(s), such as one or more of the following:

i) PVT property prediction and/or simulation (e.g., prediction and/or simulation of fluid properties of the reservoir such as phase envelope, pressure-temperature (PT) flash, constant composition expansion (CCE), differential liberation (DL), constant volume depletion (CVD), separation, viscosity, oil and gas formation volume factors (FVF), and compressibility factor);

ii) compositional and property gradient prediction;

iii) gas hydrate formation prediction;

iv) wax precipitation prediction;

v) asphaltene precipitation prediction; and vi) scaling prediction.

The equations of the EOS model(s) of step 125 for the various applications can be part of a commercially available software package, such as PVT Pro, dbrSOLIDS, and dbrHydrate, all fluid modeling softwares commercially available from DBR Technology Center, a division of Schlumberger Canada Limited, located in Edmonton, Alberta, Canada.

Examples of equations of EOS models for gas hydrate prediction are described in H. J. Ng et al., "The Measurement and Prediction of Hydrate Formation in Liquid Hydrocarbon-Water Systems," *Industrial & Engineering Chemistry Fundamentals*, 15, 293 (1976); H. J. Ng et al., "Hydrate Formation in Systems Containing Methane, Ethane, Propane, Carbon Dioxide or Hydrogen Sulfide in the Presence of Methanol," *Fluid Phase Equilibria*, 21, 145 (1985); H. J. Ng et al., "New Developments in the Measurement and Prediction of Hydrate Formation for Processing Needs," *International Conference on Natural Gas Hydrates, Annals of the New York Academy of Sciences*, Vol. 715, 450-462 (1994); J. Y. Zuo et al. "Representation of Hydrate Phase Equilibria in Aqueous Solutions of Methanol and Electrolytes Using an Equation of State," *Energy and Fuels,* 14, 19-24 (2000); and J. Y. Zuo et al., "A Thermodynamic Model for Gas Hydrates in the Presence of Salts and Methanol," *Chemical Engineering Communications,* 184, 175-192 (2001), incorporated herein by reference in their entireties.

Examples of equations of EOS models for wax precipitation prediction are described in H. Alboudwarej et al., "Effective Tuning of Wax Precipitation Models," *7th International Conference on Petroleum Phase Behavior and Fouling*, Asheville, N.C., (2006); J. Y. Zuo et al., "An improved thermodynamic model for wax precipitation from petroleum fluids," *Chemical Engineering Science,* 56, 6941 (2001); and J. Y. Zuo et al., "Wax Formation from Synthetic Oil Systems and Reservoir Fluids," 11*th International Conference on Properties and Phase Equilibria for Product and Process*

*Design*, Crete, Greece, May 20-25, (2007), incorporated herein by reference in their entireties.

In the preferred embodiment, the EOS model for wax precipitation employs a distribution of n-paraffin in crude oil. Two different methods can be used for this purpose, one for systems with experimental high temperature gas chromatography (HTGC) data and the other for systems without HTGC data. Note that HTGC allows for the direct detection and quantification of n-paraffins up to very high molecular weights (up to n-$C_{90}$). It can provide both the total n-paraffin content and its decay with carbon numbers/molecular weights. Therefore, the HTGC data are directly used to characterize n-paraffins. For systems without HTGC data, solvent precipitation programs such as UOP 46-85, available from UOP LLC of Des Plaines, Ill., USA, or any of its variants, are standard procedures that provide a good estimate of the total wax content of stock tank oil (STO). If no total wax content is available, a correlation is used to estimate it. The exponential decay ($a$) of the n-paraffins in reservoir fluids is well documented in the literature. It is defined as the ratio between the mass fractions of two successive n-paraffins, $$\alpha = \frac{wC_n}{wC_{n-1}}.$$

In the preferred embodiment, $\alpha$ is set to 0.88 as a default value. The physical properties of n-paraffins and residue are calculated by different correlations well known in the art. The improved wax model is employed to predict thermodynamic wax appearance temperature (WAT) locus of a live oil fluid. In order to observe the sensitivity of WAT to the amount of wax precipitated in the fluid, a series of wax quality lines at fixed amount of precipitated wax are calculated using the improved wax model.

An example of equations of an EOS model for asphaltene precipitation prediction is described in J. Du et al., "A Thermodynamic Model for the Predictions of Asphaltene Precipitation," *Petroleum Science and Technology*, 22, 1023 (2004), incorporated herein by reference in its entirety.

In step 127, the equations derived in step 125 are solved by a computer-implemented iteration scheme (e.g., Newton-Raphson iteration).

In step 129, the solution of the equations derived in step 127 (or data derived therefrom, such as charts and graphs) is output for presentation to a user for analysis.

In order to validate the accuracy of the methodology described herein, empirical data from the PVT database was processed according to the methodology described herein and the results compared with lab-measured gas chromatography (GC) data for more than 100 different types of fluid samples. The full fluid compositions taken from the PVT database are first lumped into DFA-like five components of $CO_2$, $C_1$, $C_2$, $C_3$-$C_5$ and $C_{6+}$ in weight percent. These are referred to as pseudo-DFA data. The pseudo-DFA data are the input of the model. Then, the pseudo-DFA data are de-lumped and characterized by the methodology as described herein, and compared with the lab-measured GC data analyzed up to C30+. The typical results are shown in FIGS. 3 to 7, where carbon number 0 denotes $CO_2$. The agreement between the delumped and GC data is good for different types of reservoir fluids.

In order to validate the accuracy of the methodology described herein for PVT property prediction, estimates for GOR, API gravity, and FVF were calculated according to the methodology described herein and compared against lab-measured GOR, API gravity, and FVF, respectively.

Figure 8:
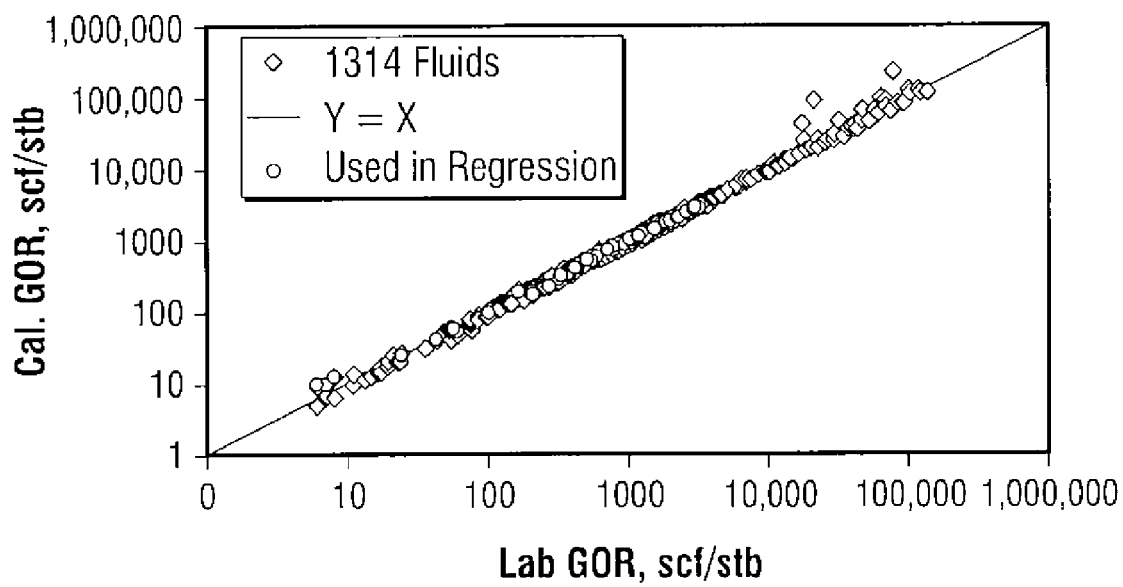
FIG. 8 is a graph that illustrates results of the reservoir fluid compositional analysis methodology described herein as compared to lab-measured GOR data for a number of different fluid samples.

The result of such analysis for GOR is shown in FIG. 8. Note that the circles of FIG. 8 denote data points used in the regression of the correlations (Equations 1-10). The diamonds are purely predictive. The absolute average deviation (AAD) is 4.90 percent for the more than 100 fluids with constant composition expansion (CCE) tests. To further validate the accuracy of the methodology described herein for PVT property prediction, estimates for GOR were calculated according to the methodology described herein and compared against lab-measured GOR data for 1314 fluids from a variety of sources. The results for 1314 fluids are also shown in FIG. 8 and the average absolute deviation (AAD) is 4.81 percent.

Figure 9:
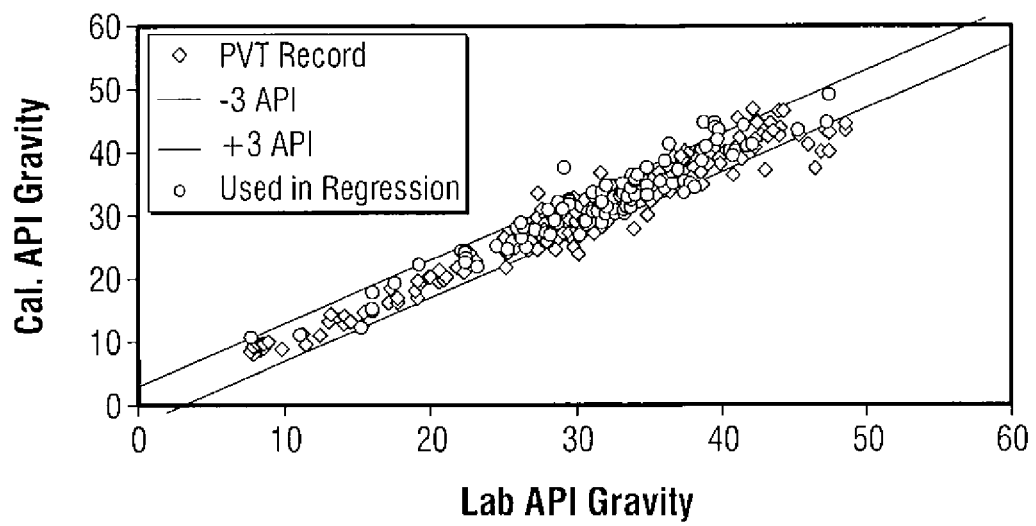
FIG. 9 is a graph that illustrates results of the reservoir fluid compositional analysis methodology described herein as compared to lab-measured API gravity data for a number of different fluid samples.

The result of such analysis of API gravity is shown in FIG. 9. Note that the open circles of FIG. 9 are the data which were used to develop the EOS model and the diamonds are the data which were not used to develop the EOS model. The absolute average deviation (AAD) is 2.5 API for the more than 300 data points.

The result of such analysis for FVF is not shown in graphical form. However, the average absolute deviation of the predicted FVF for more than 100 data points (fluids) is 1.5 percent.

Solids formation and/or precipitation, such as, gas hydrate, wax, and asphaltene are serious problems in the oil and gas industry as they may cause the plugging of wellbores, production facilities, and transportation pipelines during oil and gas production. The industry has been demanding a modular software prediction tool that is able to simulate hydrate formation, and wax and asphaltene precipitation to avoid such problems.

Figure 10:
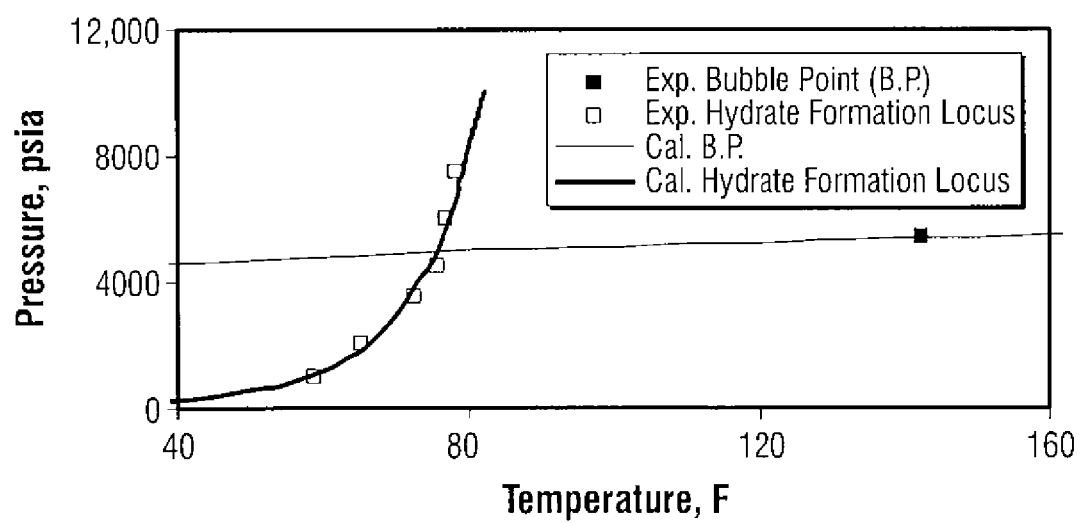
FIG. 10 is a graph that illustrates results of the methodology described herein for predicting hydrate formation for crude oil as compared to experimental data.

In order to validate the accuracy of the methodology described herein for hydrate formation prediction, the methodology described herein was used to predict hydrate formation for crude oil and compared against experimental data. The result of such analysis is shown in FIG. 10. The predictions are in good agreement with the experimental data.

Figure 11:
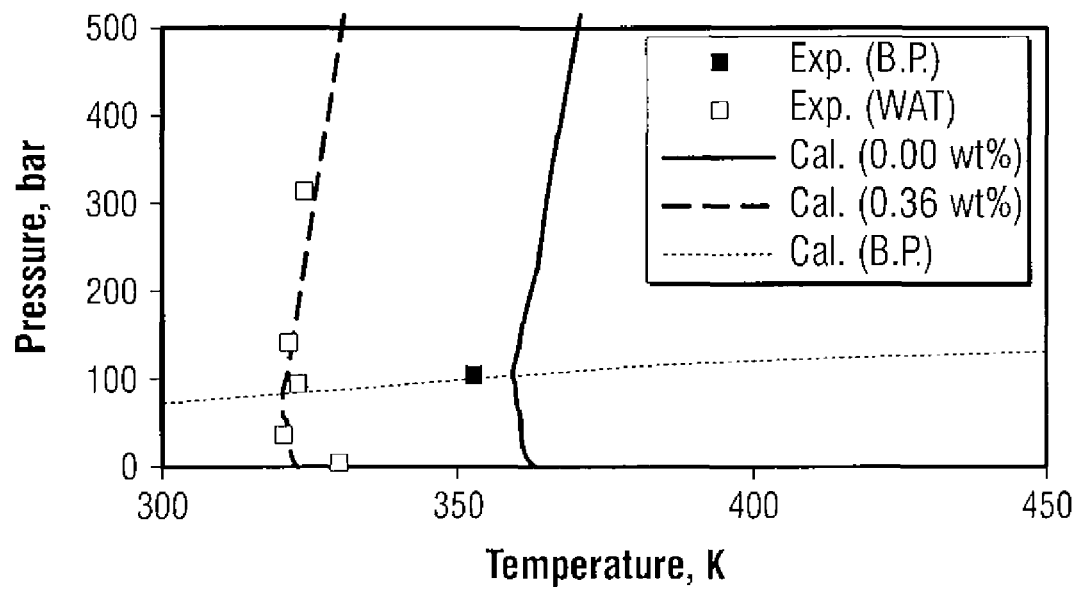
FIG. 11 is a graph that illustrates results of the methodology described herein for predicting wax precipitation as compared to experimental data.

In order to validate the accuracy of the methodology described herein for wax precipitation prediction, the methodology described herein was used to predict wax precipitation conditions for a live oil fluid and compared against experimental data. The result of such analysis is shown in FIG. 11. The EOS model for wax precipitation used in this analysis employed a distribution of n-paraffin in crude oil as described above. This model is used to predict thermodynamic wax appearance temperature (WAT) locus of the live oil fluid. In order to observe the sensitivity of WAT to the amount of wax precipitated in the fluid, a series of wax quality lines at fixed amount of precipitated wax are calculated using the improved wax model. It is found that the WAT locus can be shifted close to the measured WAT at a small amount of wax precipitated (0.36 wt %) in the fluid as shown in FIG. 11.

Figure 12:
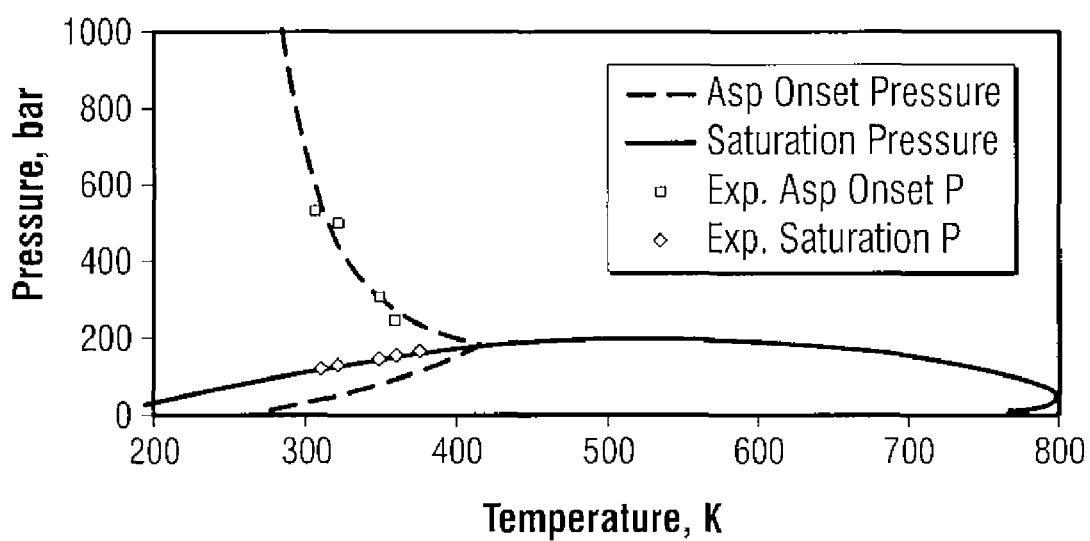
FIG. 12 is a graph that illustrates results of the methodology described herein for asphaltene precipitation conditions as compared to experimental data.

In order to validate the accuracy of the methodology described herein for asphaltene precipitation prediction, the methodology described herein was used to predict asphaltene precipitation conditions for black oil and compared against experimental data. The result of such analysis is shown in FIG. 12. The calculation results show that the proposed model gives satisfactory predictions of onset pressure over the entire experimental temperature range. The model can also be applied to a variety of systems including live oil, dead oil, bitumen, and their solvent injection systems.

Figure 13:
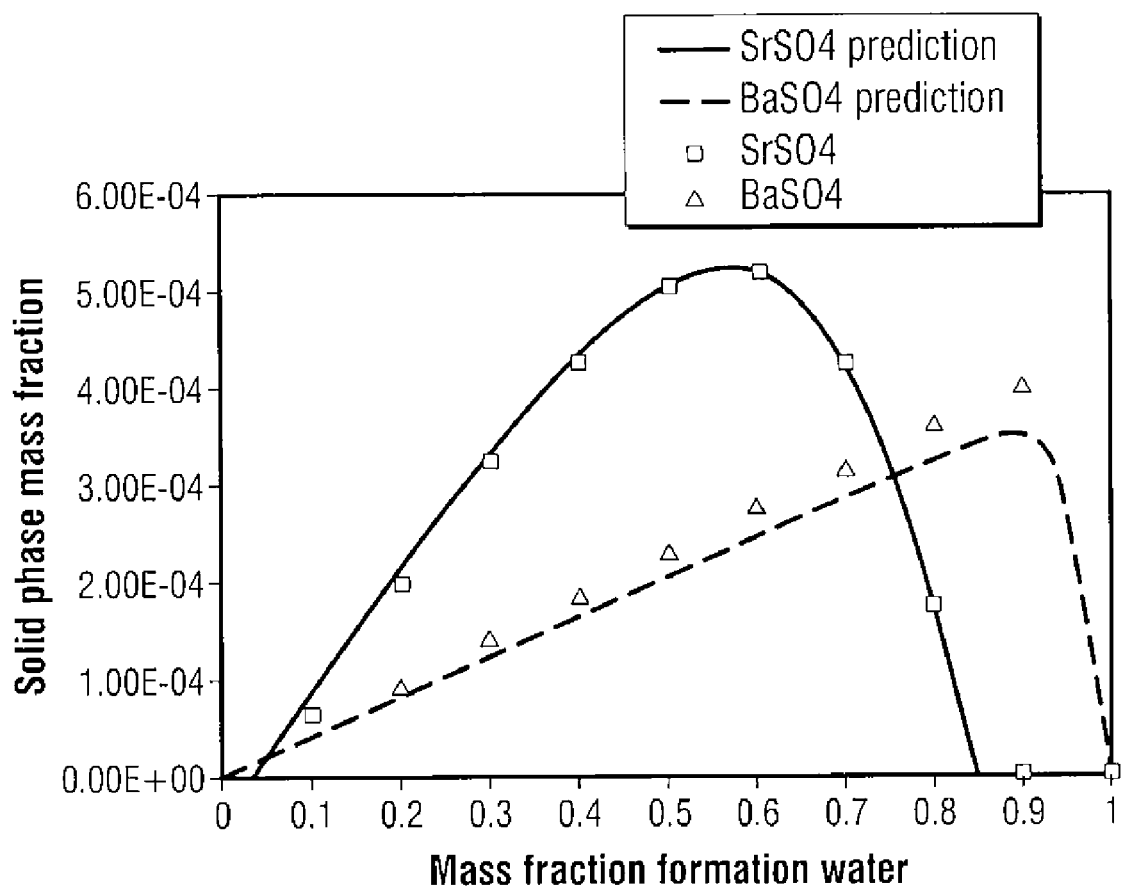
FIG. 13 is a graph that illustrates results of the methodology described herein for predicting scaling as compared to experimental data.

Inorganic scales may precipitate from produced and/or injected water, and are responsible for a significant portion of production decline. The problem will become increasingly important in the future as water cut increases and reservoir pressures decrease in the production. In order to validate the accuracy of the methodology described herein for scale precipitation prediction, the methodology described herein was preliminarily validated against available experimental data, and various scaling scenarios are simulated that demonstrate the ability of the developed model in forecasting of production problems caused by inorganic scale formation as shown in FIG. 13.

There have been described and illustrated herein a preferred embodiment of a method, system, and apparatus for characterizing the compositional components of a reservoir of interest and analyzing fluid properties of the reservoir of interest based upon its compositional components. While particular embodiments of the invention have been described, it is not intended that the invention be limited thereto, as it is intended that the invention be as broad in scope as the art will allow and that the specification be read likewise. Thus, while particular PVT databases and related PVT analysis have been disclosed, it will be appreciated that other PVT databases and PVT analysis can be used as well. In addition, while particular formulations of empirical relations have been disclosed with respect to particular alkane components, it will be understood that other empirical relations with regard to the same or other reservoir fluid components can be used. Furthermore, while particular data processing methodologies and systems have been disclosed, it will be understood that other suitable data processing methodologies and systems can be similarly used. Moreover, while particular regression analyses have been disclosed in reference to the PVT database, it will be appreciated that other regression analyses could be used as well. Also, while particular equation of state models and applications of such EOS have been disclosed for predicting properties of reservoir fluid, it will be appreciated that other equations of state and applications thereof could be used as well. It will therefore be appreciated by those skilled in the art that yet other modifications could be made to the provided invention without deviating from its scope as claimed.

What is claimed is:

1. A method for characterizing one or more properties of a multi-component petroleum fluid comprising:
    (a) measuring downhole with a downhole fluid analysis tool data representing at least one property for a group of components of the multi-component petroleum fluid and storing the data in a non-transitory, computer-readable memory, said at least one property for the group of components comprising weight percentage of the group of components;
    (b) using a computer processor and software stored in the computer-readable memory to derive at least one property for the respective components of the group of components based on the data stored in (a), wherein said at least one property comprises weight percentages for the respective components of the group, and an empirical relation derived from analysis of a pressure-volume-temperature (PVT) database, wherein said empirical relation follows a linear function of carbon number for the respective components of the group and is based on weighing factors calculated according to the equation, $\psi_i = A*CN_i + \beta$, where i varies over a range of integers corresponding to the group of single carbon number components of the group of components, $\psi_i$ is the weighing factor for the $i^{th}$ single carbon number component in the group of components, A and B are determined by a regression analysis of the PVT database, and $CN_i$ is the carbon number for the $i^{th}$ single carbon number component in the group of components;
    (c) using the computer processor and software and the at least one property for the respective components of the group derived in (b) to estimate or predict one or more properties of said multi-component fluid; and
    (d) outputting the results obtained in (c) for presentation to a user.

2. A method according to claim 1, wherein the components of the group comprise single carbon number alkanes.

3. A method according to claim 1, wherein said empirical relation is derived by normalizing said weighing factors.

4. A method according to claim 1, further comprising:
    (e) deriving at least one property for at least one particular component of the multi-component petroleum fluid based on at least one property for a respective component of the group derived in (b) and an empirical relation derived from analysis of the PVT database.

5. A method according to claim 4, wherein the at least one particular component and respective component in (e) are single carbon number hydrocarbon components with the particular component having a larger carbon number than that of the respective component.

6. A method for characterizing one or more properties of a multi-component petroleum fluid comprising:
    (a) measuring downhole with a downhole fluid analysis tool data representing at least one property for a group of components of the multi-component petroleum fluid and storing the data in a non-transitory, computer-readable memory, said at least one property for the group of components comprising weight percentage of the group of components;
    (b) using a computer processor and software stored in the computer-readable memory to derive at least one property for the respective components of the group of components based on the data stored in (a) and an empirical relation derived from analysis of a pressure-volume-temperature (PVT) database, said at least one property for the respective components of the group of components comprising weight percentages for the respective components;
    (c) deriving at least one property for at least one particular component of the multi-component petroleum fluid based on at least one property for a respective component of the group of components derived in (b) and an empirical relation derived from analysis of the PVT database, wherein said at least one property includes weight percentage of the particular component,
    (d) wherein the empirical relation follows a linear function of the form: $W_{C_T} = C*W_{C_x}$, where $W_{C_x}$ is a weight percentage for a single carbon number component derived in (b), C is a constant, and $W_{C_T}$ is the weight percentage of the particular component derived in (c)
    (e) using the computer processor and software and the at least one property for the respective components of the group of components derived in (b) to estimate or predict one or more properties of said multi-component fluid;
    (f) outputting the results obtained in (e) for presentation to a user.

7. A method according to claim 1, wherein in (c), the at least one property derived in (b) is used to generate an equation of state model for predicting one or more properties of said multi-component fluid.

8. A method according to claim 7, wherein the equation of state model predicts properties selected from the group including:
    i) PVT properties comprising phase envelope, pressure-temperature (PT) flash, constant composition expansion (CCE), differential liberation (DL), constant volume depletion (CVD), separation, viscosity, oil and gas formation volume factors (FVF), and compressibility factor;
ii) compositional and property gradients;
iii) gas hydrate formation;
iv) wax precipitation;
v) asphaltene precipitation; and
vi) scaling.

9. A method for characterizing one or more properties of a multi-component petroleum fluid comprising:
(a) using a computer processor and software stored in a non-transitory, computer-readable memory to characterize at least one property for a group of components of the multi-component petroleum fluid, the at least one property of the group including molecular weight and specific gravity, wherein molecular weight is derived by an empirical relation based on gas-oil ratio (GOR) data, and the specific gravity is derived from the molecular weight;
(b) using the computer processor and software to derive at least one property for the respective components of the group based on the at least one property for the group of components characterized in (a);
(c) using the computer processor and software and the at least one property for the respective components of the group derived in (b) to estimate or predict one or more properties of said multi-component fluid; and
(d) outputting the results obtained in (c) for presentation to a user.

10. A method according to claim 9, wherein the GOR data is measured by a downhole fluid analysis tool.

11. A method according to claim 9, wherein the OUR data is estimated from an empirical relation based on weight percentages of one or more alkane components of the multi-component petroleum fluid.

12. A method according to claim 11, wherein the empirical relation for estimating GOR is based on analysis of a pressure-volume-temperature (PVT) database.

13. A method according to claim 12, wherein the empirical relation for estimating GOR has the form $$GOR = \gamma_1 \frac{W_{C1}}{W_{C6+} - \beta_3 W_{C1}}.$$

where $W_{C1}$ and $W_{C6+}$ are the weight percentages of the C1 alkane component and C6+ alkane group, respectively, and $\gamma_1$ and $\beta_3$ are derived by correlating the GOR data to the $W_{C1}$ and $W_{C6+}$ values in the PVT database.

14. A method according to claim 12, wherein the empirical relation for estimating GOR has the form $$GOR = \gamma_2 \frac{\gamma_3 W_{C1} + \gamma_4 W_{C2-5} + \gamma_5 W_{CO2}}{W_{C6+}}.$$

where $W_{C1}$, $W_{C2-5}$, $W_{CO2}$, and $W_{C6+}$ are the weight percentages of the C1 alkane component, C2-C5 alkane group, $CO_2$ component, and C6+ alkane group, respectively, and $\gamma_2$, $\gamma^3$, $\gamma_4$, $\gamma_5$, are derived by correlating the GOR data to the $W_{CO2}$, $W_{C1}$, $W_{C2-5}$, and $W_{C6+}$ values in the PVT database.

15. A method according to claim 9, wherein the empirical relation for deriving molecular weight (MW) has the form $$MW = \alpha_1 * GOR^{\alpha_2}$$

where $\alpha_1$ and $\alpha_2$ are derived by regression analysis carried out over a pressure-volume-temperature (PVT) database.

16. A method according to claim 9, wherein the empirical relation for deriving molecular weight (MW) has the form $$MW = \beta_1 * GOR + \beta_2$$

where $\beta_1$ and $\beta_2$ are derived by regression analysis carried out over a pressure-volume-temperature (PVT) database.

17. A method according to claim 9, wherein specific gravity (SG) is derived from molecular weight (MW) by an equation of the form $$SG = \eta_1 \ln(MW) + \eta_2$$

where $\eta_1, \eta_2$ are derived by analysis of a pressure-volume-temperature (PVT) database.

18. A method according to claim 9, wherein the properties of the respective components of the group derived in (b) include weight percentages for the respective components of the group.

19. A method according to claim 18, wherein the weight percentages for the respective components of the group are derived by solving a series of equations of the form $$\ln W_{Ci} = D + E * CNi \quad (1)$$

$$\sum_{i=C7}^{Cmax} W_{Ci} = \sum_{i=C7}^{Cmax} D + E * CNi = W_{C7+} \quad (2)$$

$$\sum_{i=C7}^{Cmax} \frac{W_{Ci}}{MW_{Ci}} = \sum_{i=C7}^{Cmax} \frac{D + E * CNi}{MW_{Cj}} = \frac{W_{C7+}}{MW_{C7+}} \quad (3)$$

where $W_{Ci}$ are weight percentages for single carbon number alkane components C7 to Cmax, CNi is the carbon number for the $i^{th}$ single carbon number alkane component, $MW_{Ci}$ is the molecular weight of the single carbon number alkane component C7 to Cmax, and D and E are derived by solving Equations (2) and (3).

20. A method according to claim 9, wherein in (c), the at least one property derived in (b) is used to generate an equation of state model for predicting one or more properties of said multi-component fluid.

21. A method according to claim 20, wherein the equation of state model predicts properties selected from the group including:
i) pressure-volume-temperature (PVT) properties comprising phase envelope, pressure-temperature (PT) flash, constant composition expansion (CCE), differential liberation (DL), constant volume depletion (CVD), separation, viscosity, oil and gas formation volume factors (FVF) and compressibility factor;
ii) compositional and property gradients;
iii) gas hydrate formation;
iv) wax precipitation;
v) asphaltene precipitation; and
vi) scaling.

22. A computer processing system for characterizing one or more properties of a multi-component petroleum fluid, the system comprising:
(a) non-transitory memory, processor, and software means for characterizing at least one property for a group of components of the multi-component petroleum fluid, the at least one property of the group including molecular weight and specific gravity, wherein molecular weight is derived by an empirical relation based on gas-oil ratio (GOR) data, and the specific gravity is derived from the molecular weight;
(b) processor and software means for deriving at least one property for the respective components of the group based on the at least property for the group of components characterized in (a); and
(c) processor and software means for using the at least one property for the respective components of the group derived in (b) to estimate or predict one or more properties of said multi-component fluid.

23. A computer processing system according to claim 22, wherein the GOR data is measured by a downhole fluid analysis tool.

24. A computer processing system according to claim 22, wherein the GOR data is estimated from an empirical relation based on weight percentages of one or more alkane components of the multi-component petroleum fluid.

25. A non-transitory, computer-readable medium containing computer instructions stored therein for causing a computer processor to perform a sequence of instructions for performing method steps for characterizing one or more properties of a multi-component petroleum fluid, the method steps comprising:

(a) characterizing at least one property for a group of components of the multi-component petroleum fluid, the at least one property of the group including molecular weight and specific gravity, wherein molecular weight is derived by an empirical relation based on gas-oil ratio (GOR) data, and the specific gravity is derived from the molecular weight;
(b) deriving at least one property for the respective components of the group based on the at least property for the group of components characterized in (a); and
(c) using the at least one property for the respective components of the group derived in (b) to estimate or predict one or more properties of said multi-component fluid.

26. A non-transitory, computer-readable medium according to claim 25, wherein the GOR data is measured by a downhole fluid analysis tool.

27. A non-transitory, computer-readable medium according to claim 25, wherein the GOR data is estimated from an empirical relation based on weight percentages of one or more alkane components of the multi-component petroleum fluid.

* * * * *